United States Patent
Fischer et al.

(10) Patent No.: US 6,515,184 B1
(45) Date of Patent: Feb. 4, 2003

(54) CYCLOPENTANE-1,3-DIONE DERIVATIVES, HERBICIDAL AND PESTICIDAL COMPOSITIONS CONTAINING THEM, METHODS OF USING THEM TO COMBAT PESTS AND WEEDS AND PROCESS FOR THE PREPARATION THEREOF

(75) Inventors: Reiner Fischer, Monheim (DE); Michael Ruther, Monheim (DE); Alan Graff, Köln (DE); Arno Widdig, Odenthal (DE); Jacques Dumas, Orange, CT (US); Christoph Erdelen, Leichlingen (DE); Peter Dahmen, Neus (DE); Markus Dollinger, Leverkusen (DE); Ulrike Wachendorff-Neumann, Neuwied (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/051,185

(22) Filed: Apr. 6, 1998

Related U.S. Application Data

(63) Continuation of application No. PCT/EP96/04283, filed on Oct. 1, 1996.

(30) Foreign Application Priority Data

Oct. 13, 1995 (DE) .......................................... 195 32 218

(51) Int. Cl.[7] ..................... C07C 49/297; C09C 49/323; A01N 35/06
(52) U.S. Cl. ..................... 568/327; 568/329; 568/330; 504/161

(58) Field of Search .......................... 560/258; 568/327, 568/338, 328; 504/161

(56) References Cited

U.S. PATENT DOCUMENTS

| 4,283,348 A | 8/1981 | Wheeler | .................... 568/29 X |
| 4,551,547 A | 11/1985 | Wheeler | .................... 560/255 |

FOREIGN PATENT DOCUMENTS

| WO | WO 96 01798 | 1/1996 |
| WO | WO 96 03366 | 2/1996 |

*Primary Examiner*—Floyd D. Higel
(74) *Attorney, Agent, or Firm*—Norris McLaughlin & Marcus

(57) ABSTRACT

The present invention relates to novel bicyclic cyclopentane-1,3-dione derivatives of the formula (I)

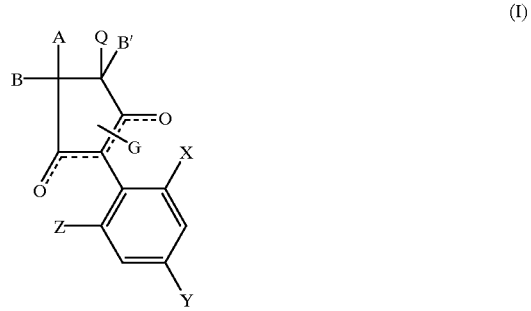

to a process for their preparation and to their use as pesticides and herbicides.

10 Claims, No Drawings

CYCLOPENTANE-1,3-DIONE DERIVATIVES, HERBICIDAL AND PESTICIDAL COMPOSITIONS CONTAINING THEM, METHODS OF USING THEM TO COMBAT PESTS AND WEEDS AND PROCESS FOR THE PREPARATION THEREOF

This application is a 371 of PCT/EP96/04283, filed Oct. 1, 1996.

The present invention relates to novel cyclopentane-1,3-dione derivatives, to processes for their preparation and to their use as herbicides and pesticides.

It is known that certain substituted 2-arylcyclopentanediones such as, for example, 2-(2',4'-dimethylphenyl)4,5,6,7,8,9-hexahydro-1,3-indandione have herbicidal and acaricidal properties (cf. for example U.S. Pat. Nos. 4,283,348; 4,338,122; 4,436,666; 4,526,723; 4,551,547 and 4,626,698). Moreover, 2-(2,4,6-trimethylphenyl)-1,3-indandione is known from the publication J. Economic Entomology, 66, (1973), 584 and the published specification DE 2 361 084, and herbicidal and acaricidal activities are mentioned.

Furthermore, WO 96/01 798 and WO 96/03 366 describe the use of 2-aryl-cyclopentane-1,3-dione derivatives as herbicides and pesticides.

However, the activity of these prior art compounds, in particular at low application weights and concentrations, is not satisfactory in all areas of use. Furthermore, the known compounds do not always have sufficient plant safety with respect to crops.

This invention, accordingly, provides novel bicyclic cyclopentane-1,3-dione derivatives of the formula (I)

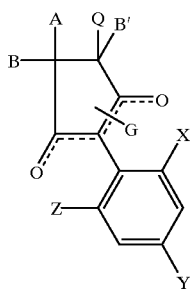

(I)

in which
X represents halogen, alkyl, alkenyl, alkoxy, alkenyloxy, alkylthio, alkylsulphinyl, alkylsulphonyl, halogenoalkyl, halogenoalkoxy, halogenoalkenyloxy, nitro, cyano or respectively optionally substituted phenyl, phenoxy, phenylthio, benzyloxy or benzylthio,
Y represents hydrogen, halogen, alkyl, alkenyl, alkoxy, alkenyloxy, alkylthio, alkylsulphinyl, alkylsulphonyl, halogenoalkyl, halogenoalkoxy, halogenoalkenyloxy, nitro or cyano,
Z represents halogen, alkyl, alkenyl, alkoxy, alkenyloxy, halogenoalkyl, halogenoalkoxy, halogenoalkenyloxy, nitro or cyano, with the proviso that X, Y and Z may not simultaneously represent methyl;
A and Q together represent alkanediyl or alkenediyl, each of which is optionally substituted by halogen, hydroxyl, mercapto, by respectively optionally substituted alkyl, alkoxy, alkylthio, cycloalkyl, benzyloxy or aryl, and which may additionally contain one of the groups below

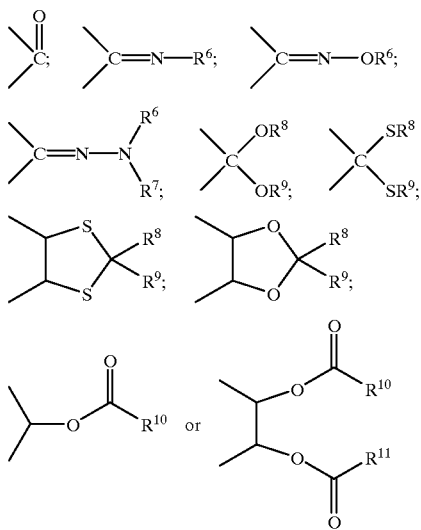

or may be bridged by an alkanediyl group,
B and B' independently of one another each represent hydrogen, halogen or alkyl or together represent respectively optionally substituted alkanediyl or alkenediyl,
G represents hydrogen (a) or one of the groups

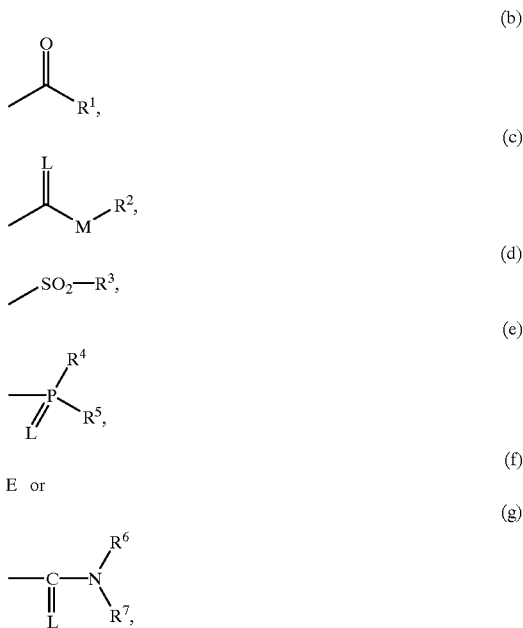

in which
E represents a metal ion equivalent or an ammonium ion,
L represents oxygen or sulphur and
M represents oxygen or sulphur,
$R^1$ represents respectively optionally substituted alkyl, alkenyl, alkoxyalkyl, alkylthioalkyl, polyalkoxyalkyl or cycloalkyl, which may contain at least one hetero atom, respectively optionally substituted phenyl, phenylalkyl, hetaryl, phenoxyalkyl or hetaryloxyalkyl, R² represents respectively optionally substituted alkyl, cycloalkyl, alkenyl, alkoxyalkyl, polyalkoxyalkyl, phenyl or benzyl, R³, R⁴ and R⁵ independently of one another each represent respectively optionally halogen-substituted alkyl, alkoxy, alkylamino, dialkylamino, alkylthio, alkenylthio, cycloalkylthio or represent respectively optionally substituted phenyl, phenylalkyl, phenoxy or phenylthio, R⁶ represents hydrogen, respectively optionally halogen-substituted alkyl, alkenyl, alkoxyalkyl, represents respectively optionally substituted cycloalkyl, phenyl or benzyl, R⁷ represents hydrogen or represents respectively optionally halogen-substituted alkyl or alkenyl or R⁶ and R⁷ combine with the linking N-atom to form an optionally oxygen- or sulphur-containing and optionally substituted ring, R⁸ and R⁹ independently of one another each represent hydrogen or respectively optionally substituted alkyl, phenyl or phenylalkyl, or together represent an optionally substituted alkanediyl radical and R¹⁰ and R¹¹ independently of one another each represent respectively optionally halogen-substituted alkyl, alkenyl, alkoxy, alkylamino, dialkylamino, alkenylamino or dialkenylamino or respectively optionally substituted phenyl or benzyl.

Depending on the position of the substituent G, the compounds of the formula (I) can be present in the two isomeric forms of the formulae (I-A) and (I-B), which is meant to be expressed by the dotted line in the formula (I):

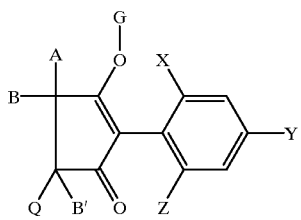
(I-A)

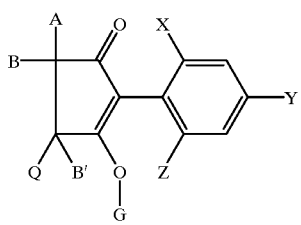
(I-B)

The compounds of the formulae (I-A) and (I-B) can be present both as mixtures and in the form of their pure isomers. Mixtures of the compounds of the formulae (I-A) and (I-B) may optionally be separated by physical methods, for example by chromatographic methods.

For reasons of clarity, hereinbelow only one of the possible isomers is shown in each case. It is implied that the compound in question may be present as a mixture of isomers or in the respective other isomeric form.

Including the various meanings (a), (b), (c), (d), (e), (f) and (g) of group G, the following principle structures (Ia) to (Ig) result:

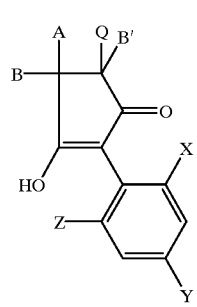
(Ia)

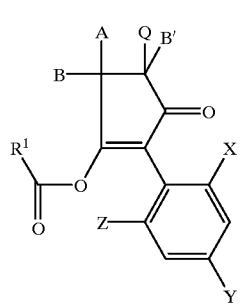
(Ib)

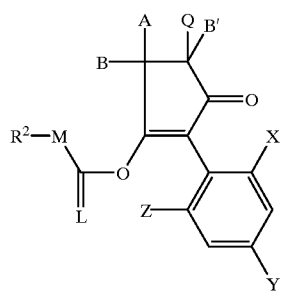
(Ic)

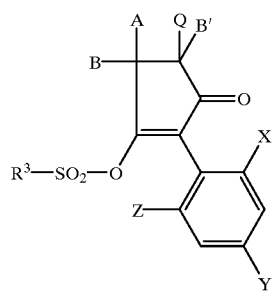
(Id)

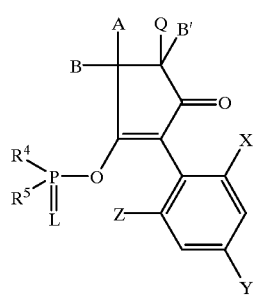
(Ie)

-continued (If)

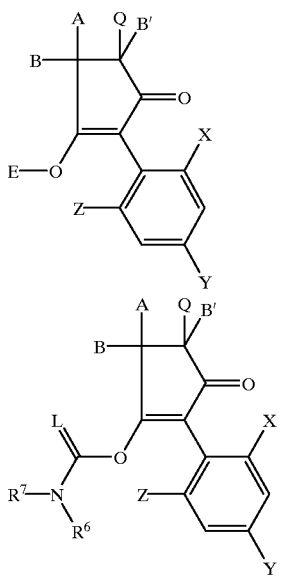

(Ig)

in which
A, B, B', E, L, M, Q, X, Y, Z, $R^1$, $R^2$, $R^3$, $R^4$, $R^5$, $R^6$ and $R^7$ are each as defined above.

Owing to one or more chiral centres, the compounds of the formula (Ia)–(Ig) are generally obtained as a mixture of stereoisomers. They may be present and used both in the form of their diastereomer mixtures and as pure diastereomers or enantiomers.

Furthermore, it has been found that the novel substituted cyclopentane-1,3-dione derivatives of the formula (I) are obtained by one of the processes described below.

(A) Cyclopentane-1,3-diones or enols thereof of the formula (Ia)

(Ia)

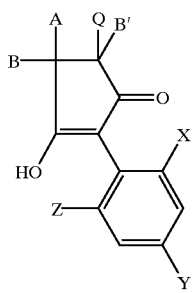

in which
A, B, B', Q, X, Y and Z are each as defined above
are obtained
when 5-aryl-4-keto-valerates of the formula (II)

(II)

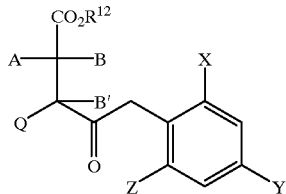

in which
A, B, B', Q, X, Y and Z are each as defined above, and $R^{12}$ represents alkyl (preferably $C_1$–$C_6$-alkyl)
are condensed intramolecularly in the presence of a diluent and in the presence of a base;
and (B) compounds of the formula (Ib)

(Ib)

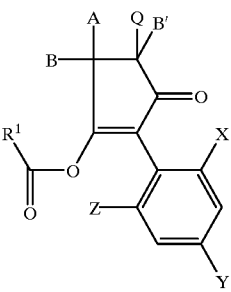

in which
A, B, B', Q, X, Y, Z and $R^1$ are each as defined above
are obtained
when compounds of the formula (Ia)

(Ia)

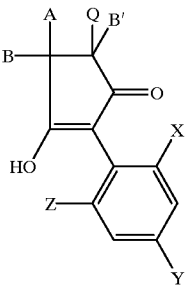

in which
A, B, B', X, Y, Z and Q are each as defined above
are reacted

α) with acyl halides of the formula (III)

(III)

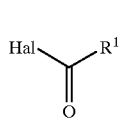

in which
$R^1$ is as defined above and
Hal represents halogen (in particular chlorine and bromine),
if appropriate in the presence of a diluent and if appropriate in the presence of an acid binder
or β) with carboxylic anhydrides of the formula (IV)

$R^1$—CO—O—CO—$R^1$ (IV)

in which
$R^1$ is as defined above,
if appropriate in the presence of a diluent and if appropriate in the presence of an acid binder;
and (C) compounds of the formula (Ic-1)

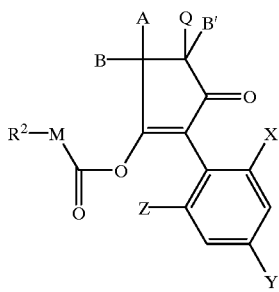
(Ic-1)

in which
A, B, B', Q, X, Y, Z and R² are as defined above
and
M represents oxygen or sulphur
are obtained
when compounds of the formula (Ia)

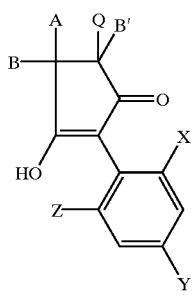
(Ia)

in which
A, B, B', Q, X, Y and Z are each as defined above
are reacted with chloroformic esters or chloroformic thioesters of the formula (V)

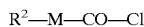
R²—M—CO—Cl    (V)

in which
R² and M are each as defined above,
if appropriate in the presence of a diluent and if appropriate in the presence of an acid binder;
and
(D) compounds of the formula (Ic-2)

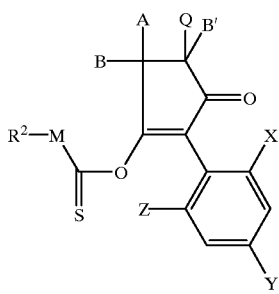
(Ic-2)

in which
A, B, B', Q, X, Y, Z and R² are each as defined above,
and
M represents oxygen or sulphur,
are obtained, when compounds of the formula (Ia)

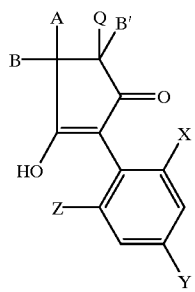
(Ia)

in which
A, B, B', Q, X, Y and Z are each as defined above
are reacted

α) with chloromonothioformic esters or chlorodithioformic esters of the formula (VI)

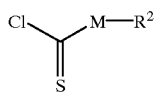
(VI)

in which
M and R² are each as defined above,
if appropriate in the presence of a diluent and if appropriate in the presence of an acid binder,
or β) with carbon disulphide and then with alkyl halides of the general formula (VII)

R²-Hal    (VII)

in which
R² is as defined above
and
Hal represents chlorine, bromine or iodine,
if appropriate in the presence of a diluent and if appropriate in the presence of a base;
and (E) compounds of the formula (Id)

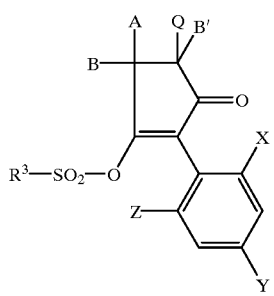
(Id)

in which
A, B, B', Q, X, Y, Z and R³ are each as defined above
are obtained when compounds of the formula (Ia)

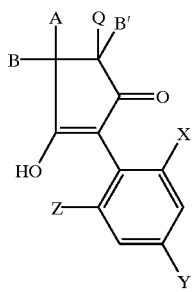
(Ia)

in which
A, B, B', Q, X, Y and Z are each as defined above
are reacted with sulphonyl chlorides of the formula (VIII)

$R^3$—$SO_2$—Cl  (VIII)

in which
$R^3$ is as defined above,
if appropriate in the presence of a diluent and if appropriate in the presence of an acid binder;
and (F) compounds of the formula (Ie)

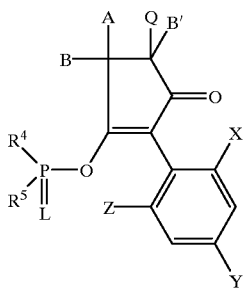
(Ie)

in which
A, B, L, B', Q, X, Y, Z, $R^4$ and $R^5$ are each as defined above
are obtained
when compounds of the formula (Ia) or enols thereof

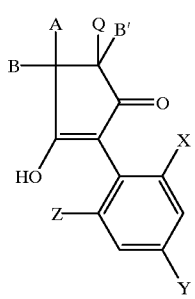
(Ia)

in which
A, B, B', Q, X, Y and Z are each as defined above are reacted with phosphorus compounds of the formula (IX)

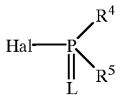
(IX)

in which
L, $R^4$ and $R^5$ are each as defined above
and
Hal represents halogen, (in particular chlorine and bromine)
if appropriate in the presence of a diluent and if appropriate in the presence of an acid binder;
and (G) compounds of the formula (If)

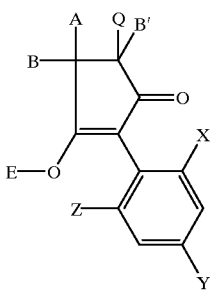
(If)

in which
A, B, B', Q, X, Y and Z are each as defined above
and
E represents a metal ion equivalent or represents an ammonium ion
are obtained
when compounds of the formula (Ia)

(Ia)

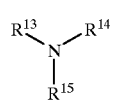

in which
A, B, B', Q, X, Y and Z are each as defined above
are reacted with metal compounds or amines of the formulae (X) and (XI), respectively Me $R_t^{16}$  (X)

$R^{13}$\N/$R^{14}$  (XI)
      |
      $R^{15}$ in which
Me represents mono- or bivalent metal ions (in particular of lithium, sodium, potassium, magnesium or calcium), t represents the number 1 or 2, $R^{13}$, $R^{14}$ and $R^{15}$ independently of one another each represent hydrogen or alkyl (in particular $C_1$–$C_8$-alkyl) and $R^{16}$ represents hydrogen, hydroxyl or $C_1$–$C_4$-alkoxy, if appropriate in the presence of a diluent.

(H) Furthermore, it has been found that compounds of the formula (Ig)

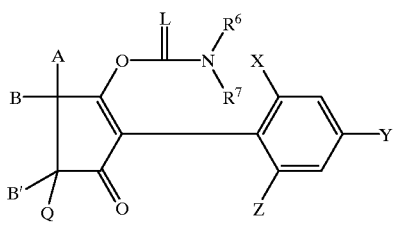

in which

A, B, L, B', Q, X, Y, Z, $R^6$ and $R^7$ are each as defined above are obtained when compounds of the formula (Ia)

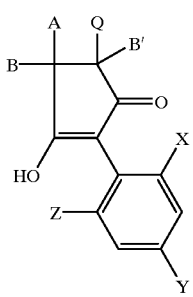

in which

A, B, B', Q, X, Y and Z are each as defined above are reacted

α) with compounds of the formula (XII)

$$R^6-N=C=L \qquad (XII)$$

in which

L and $R^6$ are each as defined above, if appropriate in the presence of a diluent and if appropriate in the presence of a catalyst or β) with carbamoyl chlorides or thiocarbamoyl chlorides of the formula (XIII)

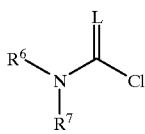

in which

L, $R^6$ and $R^7$ are each as defined above if appropriate in the presence of a diluent and if appropriate in the presence of an acid binder.

Furthermore, it has been found that the novel compounds of the formula (I) have outstanding insecticidal, acaricidal and herbicidal action.

The formula (I) provides a definition of the compounds according to the invention. Preferred substituents or ranges of the radicals listed in the formulae mentioned hereinabove and hereinbelow are illustrated below.

X preferably represents halogen, $C_1$–$C_6$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_1$–$C_6$-halogenoalkoxy, $C_2$–$C_6$-halogenoalkenyloxy, nitro, cyano or respectively optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, benzyloxy or benzylthio.

Y preferably represents hydrogen, halogen, $C_1$–$C_6$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_1$–$C_6$-halogenoalkoxy, $C_2$–$C_6$-halogenoalkenyloxy, nitro or cyano.

Z preferably represents halogen, $C_1$–$C_6$-alkyl, $C_2$–$C_6$-alkenyl, $C_1$–$C_6$-alkoxy, $C_2$–$C_6$-alkenyloxy, $C_1$–$C_6$-halogenoalkyl, $C_1$–$C_6$-halogenoalkoxy, $C_2$–$C_6$-halogenoalkenyloxy, nitro or cyano.

A and Q together preferably represent $C_1$–$C_6$-alkanediyl or $C_2$–$C_6$-alkenediyl, each of which is optionally mono- to trisubstituted by identical or different substituents from the group consisting of halogen, hydroxyl, mercapto, and of $C_1$–$C_{10}$-alkyl, $C_1$–$C_6$-alkoxy, $C_1$–$C_6$-alkylthio, $C_3$–$C_7$-cycloalkyl, each of which is optionally mono- to nonasubstituted by identical or different halogens, and of benzyloxy and phenyl, each of which is optionally mono- to pentasubstituted by identical or different substituents from the group consisting of halogen, $C_1$–$C_6$-alkyl and $C_1$–$C_6$-alkoxy, it being additionally possible for the $C_1$–$C_6$-alkanediyl or the $C_2$–$C_6$-alkenediyl to contain one of the groups below

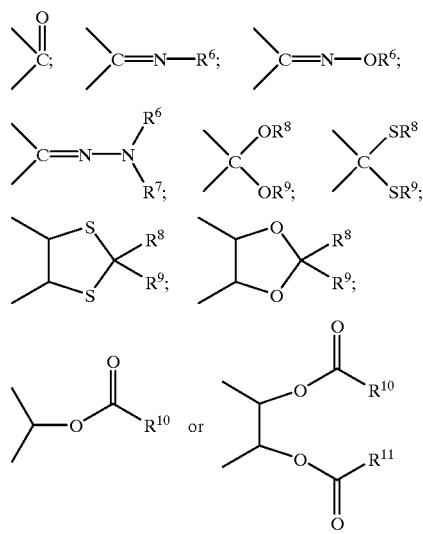

or to be bridged by a $C_1$–$C_2$-alkanediyl group.

B and B' independently of one another each preferably represent hydrogen, halogen or $C_1$–$C_6$-alkyl or together preferably represent respectively optionally $C_1$–$C_6$-alkyl-substituted $C_1$–$C_6$-alkanediyl or $C_2$–$C_4$-alkenediyl.

G preferably represents hydrogen (a) or represents one of the groups

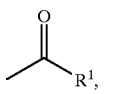
(b)

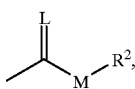
(c)

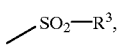
(d)

(e)
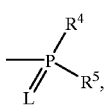

E or (f)

(g)
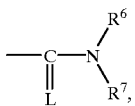

in which
E represents a metal ion equivalent or an ammonium ion,
L represents oxygen or sulphur and
M represents oxygen or sulphur.

$R^1$ preferably represents $C_1-C_{20}$-alkyl, $C_2-C_{10}$-alkenyl, $C_1-C_8$-alkoxy-$C_1-C_8$-alkyl, $C_1-C_8$-alkylthio-$C_1-C_8$-alkyl, poly-$C_1-C_8$-alkoxy-$C_1-C_8$-alkyl, each of which is optionally mono- or polysubstituted by identical or different halogens, or preferably represents $C_3-C_8$-cycloalkyl which is optionally mono- or polysubstituted by identical or different substituents from the group consisting of halogen, $C_1-C_6$-alkyl and $C_1-C_6$-alkoxy and in which at least one methylene group may be replaced by an oxygen and/or sulphur atom, preferably represents phenyl which is optionally mono- or polysubstituted by identical or different substituents from the group consisting of halogen, nitro, cyano, $C_1-C_6$-alkyl, $C_1-C_6$-alkoxy, $C_1-C_6$-halogenoalkyl and $C_1-C_6$-halogenoalkoxy, preferably represents phenyl-$C_1-C_6$-alkyl which is optionally mono- or polysubstituted by identical or different substituents from the group consisting of halogen, $C_1-C_6$-alkyl, $C_1-C_6$-alkoxy, $C_1-C_6$-halogenoalkyl and $C_1-C_6$-halogenoalkoxy, preferably represents hetaryl which is optionally mono- or polysubstituted by identical or different substituents from the group consisting of halogen and $C_1-C_6$-alkyl and has 5 or 6 ring atoms and one to three hetero atoms from the group consisting of oxygen, sulphur and nitrogen, preferably represents phenoxy-$C_1-C_6$-alkyl which is optionally mono- or polysubstituted by identical or different substituents from the group consisting of halogen and $C_1-C_6$-alkyl, or preferably represents hetaryloxy-$C_1-C_6$-alkyl which is optionally mono- or polysubstituted by identical or different substituents from the group consisting of halogen, amino and $C_1-C_6$-alkyl and has 5 or 6 ring atoms and one to three hetero atoms from the group consisting of oxygen, sulphur and nitrogen.

$R^2$ preferably represents $C_1-C_{20}$-alkyl, $C_2-C_{10}$-alkenyl, $C_1-C_8$-alkoxy-$C_2-C_8$-alkyl or poly-$C_1-C_8$-alkoxy-$C_1-C_8$-alkyl, each of which is optionally mono- or polysubstituted by identical or different halogens, preferably represents $C_3-C_6$-cycloalkyl which is optionally mono- or poly-substituted by identical or different substituents from the group consisting of halogen, $C_1-C_6$-alkyl and $C_1-C_6$-alkoxy, or preferably represents phenyl or benzyl, each of which is optionally mono- or polysubstituted by identical or different substituents from the group consisting of halogen, nitro, cyano, $C_1-C_6$-alkyl, $C_1-C_6$-alkoxy, $C_1-C_3$-halogenoalkoxy and $C_1-C_3$-halogenoalkyl.

$R^3$ preferably represents $C_1-C_{12}$-alkyl, each of which is optionally mono- or polysubstituted by identical or different halogens, or preferably represents phenyl or phenyl-$C_1-C_4$-alkyl, each of which is optionally mono- or polysubstituted by identical or different substituents from the group consisting of halogen, $C_1-C_6$-alkyl, $C_1-C_6$-alkoxy, $C_1-C_3$-halogenoalkyl, $C_1-C_3$-halogenoalkoxy, cyano and nitro.

$R^4$ and $R^5$ independently of one another each preferably represent $C_1-C_8$-alkyl, $C_1-C_8$-alkoxy, $C_1-C_8$-alkylamino, di-($C_1-C_8$-alkyl)-amino, $C_1-C_8$-alkylthio, $C_3-C_5$-alkenylthio, $C_3-C_7$-cycloalkylthio, each of which is optionally mono- or polysubstituted by identical or different halogens, or preferably represents phenyl, phenoxy or phenylthio, each of which is optionally mono- or polysubstituted by identical or different substituents from the group consisting of halogen, nitro, cyano, $C_1-C_4$-alkoxy, $C_1-C_4$-halogenoalkoxy, $C_1-C_4$-alkylthio, $C_1-C_4$-halogenoalkylthio, $C_1-C_4$-alkyl and $C_1-C_4$-halogenoalkyl.

$R^6$ preferably represents hydrogen, preferably represents $C_1-C_{10}$-alkyl, $C_3-C_8$-alkenyl, $C_1-C_8$-alkoxy-$C_2-C_8$-alkyl, each of which is optionally mono- or polysubstituted by identical or different halogens, preferably represents $C_3-C_{10}$-cycloalkyl which is optionally mono- or polysubstituted by identical or different substituents from the group consisting of halogen, $C_1-C_6$-alkyl, $C_1-C_6$-alkoxy, $C_1-C_3$-halogenoalkyl and $C_1-C_3$-halogenoalkoxy, preferably represents phenyl which is optionally mono- or polysubstituted by identical or different substituents from the group consisting of halogen, $C_1-C_3$-halogenoalkyl, $C_1-C_8$-alkyl, $C_1-C_3$-halogenoalkoxy and $C_1-C_8$-alkoxy, or preferably represents benzyl which is optionally mono- or polysubstituted by identical or different substituents from the group consisting of halogen, $C_{114}$ $_{C8}$-alkyl, $C_1-C_3$-halogenoalkyl, $C_1-C_3$-halogenoalkoxy and $C_1-C_8$-alkoxy.

$R^7$ preferably represents hydrogen or preferably represents $C_1-C_{10}$-alkyl or $C_3-C_{10}$-alkenyl, each of which is optionally mono- or polysubstituted by identical or different halogens, or $R^6$ and $R^7$ preferably combine with the linking N-atom to form an optionally oxygen- or sulphur-containing and optionally $C_1-C_6$-alkyl-substituted 3- to 7-membered ring.

$R^8$ and $R^9$ independently of one another each preferably represent hydrogen, preferably represent $C_1-C_6$-alkyl which is optionally mono- or polysubstituted by identical or different halogens or preferably represent phenyl or phenyl-$C_1-C_4$-alkyl, each of which is optionally mono- or polysubstituted by identical or different substituents from the group consisting of halogen, $C_1$–$C_6$-alkyl, $C_1$–$C_6$-alkoxy, $C_1$–$C_6$-halogenoalkyl, $C_1$–$C_6$-halogenoalkoxy, nitro and cyano, or together preferably represent $C_2$–$C_6$-alkanediyl which is optionally mono- or polysubstituted by identical or different substituents from the group consisting of halogen, $C_1$–$C_6$-alkyl, $C_1$–$C_6$-alkoxy and $C_1$–$C_3$-halogenoalkyl, and $R^{10}$ and $R^{11}$ independently of one another each preferably represent $C_1$–$C_{10}$-alkyl, $C_2$–$C_{10}$-alkenyl, $C_1$–$C_{10}$-alkoxy, $C_1$–$C_{10}$-alkylamino, di-($C_1$–$C_{10}$-alkyl)-amino, $C_3$–$C_{10}$-alkenylamino, di-($C_3$–$C_{10}$-alkenyl)-amino, each of which is optionally mono- or polysubstituted by identical or different halogens, or preferably represent phenyl or benzyl, each of which is mono- or polysubstituted by identical or different substituents from the group consisting of halogen, $C_1$–$C_4$-alkyl, $C_1$–$C_4$-alkoxy, $C_1$–$C_4$-halogenoalkyl, nitro and cyano.

X particularly preferably represents fluorine, chlorine, bromine, $C_1$–$C_4$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulphinyl, $C_1$–$C_4$-alkylsulphonyl, $C_1$–$C_4$-halogenoalkyl, $C_1$–$C_4$-halogenoalkoxy, $C_2$–$C_4$-halogenoalkenyloxy, nitro, cyano or particularly preferably represents respectively optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy, phenylthio, benzyloxy or benzylthio.

Y particularly preferably represents hydrogen, fluorine, chlorine, bromine, $C_1$–$C_4$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulphinyl, $C_1$–$C_4$-alkylsulphonyl, $C_1$–$C_4$-halogenoalkyl, $C_1$–$C_4$-halogenoalkoxy, $C_2$–$C_4$-halogenoalkenyloxy, nitro or cyano.

Z particularly preferably represents fluorine, chlorine, bromine, $C_1$–$C_4$-alkyl, $C_2$–$C_4$-alkenyl, $C_1$–$C_4$-alkoxy, $C_2$–$C_4$-alkenyloxy, $C_1$–$C_4$-halogenoalkyl, $C_1$–$C_4$-halogenoalkoxy, $C_2$–$C_4$-halogenoalkenyloxy, nitro or cyano.

A and Q together particularly preferably represent $C_1$–$C_5$-alkanediyl or $C_2$–$C_5$-alkenediyl, each of which is optionally mono- or disubstituted by identical or different substituents from the group consisting of fluorine, chlorine, bromine, hydroxyl, mercapto, and of $C_1$–$C_8$-alkyl, $C_1$–$C_4$-alkoxy, $C_1$–$C_4$-alkylthio, $C_5$–$C_7$-cycloalkyl or phenyl, each of which is optionally mono- to pentasubstituted by identical or different substituents from the group consisting of fluorine and chlorine, it being additionally possible for the $C_1$–$C_5$-alkanediyl or the $C_2$–$C_5$-alkenediyl to contain one of the groupings below

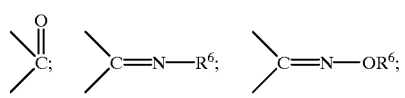

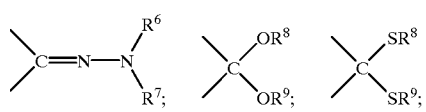

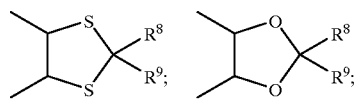

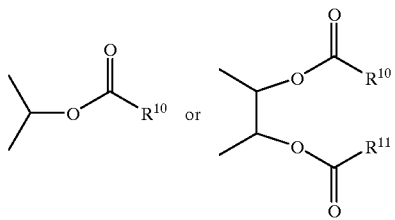

or to be bridged by a $C_1$–$C_2$-alkanediyl group.

B and B' independently of one another each particularly preferably represent hydrogen fluorine, chlorine or $C_1$–$C_4$-alkyl or together particularly preferably represent respectively optionally $C_1$–$C_4$-alkyl-substituted $C_1$–$C_5$-alkanediyl or $C_2$–$C_4$-alkenediyl.

G particularly preferably represents hydrogen (a) or particularly preferably represents one of the groups (b)

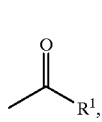

(c)

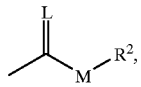

(d)

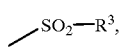

(e)

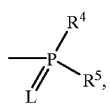

(f)

E or (g)

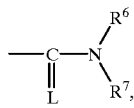

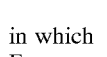

in which

E represents a metal ion equivalent or an ammonium ion,

L represents oxygen or sulphur and

M represents oxygen or sulphur.

$R^1$ particularly preferably represents $C_1$–$C_{16}$-alkyl, $C_2$–$C_8$-alkenyl, $C_1$–$C_6$-alkoxy-$C_1$–$C_6$-alkyl, $C_1$–$C_6$-alkylthio-$C_1$–$C_6$-alkyl, poly-$C_1$–$C_6$-alkoxy-$C_1$–$C_6$-alkyl, each of which is optionally mono- to nonasubstituted by identical or different substituents from the group consisting of fluorine and chlorine, or particularly preferably represents $C_3$–$C_7$-cycloalkyl which is optionally mono- to trisubstituted by identical or different substituents from the group consisting of fluorine, chlorine, $C_1$–$C_4$-alkyl and $C_1$–$C_4$-alkoxy and in which one or two not directly adjacent methylene groups may be replaced by oxygen and/or sulphur atoms, particularly preferably represents phenyl which is optionally mono- to trisubstituted by identical or different substituents from the group consisting of fluorine, chlorine, bromine, cyano, nitro, $C_1$–$C_4$-alkyl, $C_1$–$C_4$-alkoxy, $C_1$–$C_3$-halogenoalkyl and $C_1$–$C_3$-halogenoalkoxy, particularly preferably represents phenyl-$C_1$–$C_4$-alkyl which is optionally mono- to trisubstituted by identical or different substituents from the group consisting of fluorine, chlorine, bromine, $C_1$–$C_4$-alkyl, $C_1$–$C_4$-alkoxy, $C_1$–$C_3$-halogenoalkyl and $C_1$–$C_3$-halogenoalkoxy, particularly preferably represents furanyl, thienyl, pyridyl, pyrimidyl, thiazolyl or pyrazolyl, each of which is optionally mono- or disubstituted by identical or different substituents from the group consisting of fluorine, chlorine, bromine and $C_1$–$C_4$-alkyl, particularly preferably represents phenoxy-$C_1$–$C_5$-alkyl which is optionally mono- to trisubstituted by identical or different substituents from the group consisting of fluorine, chlorine and $C_1$–$C_4$-alkyl, or particularly preferably represents pyridyloxy-$C_1$–$C_6$-alkyl, pyrimidinyloxy-$C_1$–$C_6$-alkyl or thiazolyloxy-$C_1$–$C_6$-alkyl, each of which is optionally mono- or disubstituted by identical or different substituents from the group consisting of fluorine, chlorine, amino and $C_1$–$C_4$-alkyl.

$R^2$ particularly preferably represents $C_1$–$C_{16}$-alkyl, $C_2$–$C_8$-alkenyl, $C_1$–$C_6$-alkoxy-$C_2$–$C_6$-alkyl or poly-$C_1$–$C_6$-alkoxy-$C_2$–$C_6$-alkyl, each of which is optionally mono- to heptasubstituted by identical or different substituents from the group consisting of fluorine and chlorine, particularly preferably represents $C_3$–$C_6$-cycloalkyl which is optionally mono- to trisubstituted by identical or different substituents from the group consisting of fluorine, chlorine, $C_1$–$C_4$-alkyl and $C_1$–$C_4$-alkoxy, or particularly preferably represents phenyl or benzyl, each of which is optionally mono- to trisubstituted by identical or different substituents from the group consisting of fluorine, chlorine, bromine, nitro, cyano, $C_1$–$C_4$-alkyl, $C_1$–$C_4$-alkoxy, $C_1$–$C_2$-halogenoalkoxy and $C_1$–$C_2$-halogenoalkyl.

$R^3$ particularly preferably represents $C_1$–$C_9$-alkyl, which is optionally mono- to pentasubstituted by identical or different substituents from the group consisting of fluorine and chlorine, or particularly preferably represents phenyl or phenyl-$C_1$–$C_2$-alkyl, each of which is optionally mono- to trisubstituted by identical or different substituents from the group consisting of fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano and nitro.

$R^4$ and $R^5$ independently of one another each particularly preferably represent $C_1$–$C_6$-alkyl, $C_1$–$C_6$-alkoxy, $C_1$–$C_6$-alkylamino, di-($C_1$–$C_6$-alkyl)-amino, $C_1$–$C_6$-alkylthio, $C_3$–$C_4$-alkenylthio, $C_3$–$C_6$-cycloalkylthio, each of which is optionally mono- to pentasubstituted by identical or different substituents from the group consisting of fluorine and chlorine, or particularly preferably represents phenyl, phenoxy or phenylthio, each of which is optionally mono- to trisubstituted by identical or different substituents from the group consisting of fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl and $C_1$–$C_3$-halogenoalkyl.

$R^6$ particularly preferably represents hydrogen, particularly preferably represents $C_1$–$C_8$-alkyl, $C_3$–$C_6$-alkenyl, $C_1$–$C_6$-alkoxy-$C_2$–$C_6$-alkyl, each of which is optionally mono- to pentasubstituted by identical or different substituents from the group consisting of fluorine and chlorine, particularly preferably represents $C_3$–$C_8$-cycloalkyl which is optionally mono- to trisubstituted by identical or different substituents from the group consisting of fluorine, chlorine, $C_1$–$C_4$-alkyl, $C_1$–$C_4$-alkoxy, $C_1$–$C_2$-halogenoalkyl and $C_1$–$C_2$-halogenoalkoxy, particularly preferably represents phenyl which is optionally mono- to trisubstituted by identical or different substituents from the group consisting of fluorine, chlorine, bromine, $C_1$–$C_2$-halogenoalkyl, $C_1$–$C_5$-alkyl, $C_1$–$C_2$-halogenoalkoxy and $C_1$–$C_5$-alkoxy, or particularly preferably represents benzyl which is optionally mono- to trisubstituted by identical or different substituents from the group consisting of fluorine, chlorine, bromine, $C_1$–$C_5$-alkyl, $C_1$–$C_2$-halogenoalkyl, $C_1$–$C_2$-halogenoalkoxy and $C_1$–$C_5$-alkoxy.

$R^7$ particularly preferably represents hydrogen or particularly preferably represents $C_1$–$C_8$-alkyl or $C_3$–$C_8$-alkenyl, each of which is optionally mono- to pentasubstituted by identical or different substituents from the group consisting of fluorine and chlorine, or $R^6$ and $R^7$ particularly preferably combine with the linking N-atom to form an optionally oxygen- or sulphur-containing and optionally $C_1$–$C_4$-alkyl-substituted 4- to 7-membered ring.

$R^8$ and $R^9$ independently of one another each particularly preferably represent hydrogen, $C_1$–$C_4$-alkyl which is optionally mono- to pentasubstituted by identical or different substituents from the group consisting of fluorine and chlorine, or particularly preferably represent phenyl which is optionally mono- to trisubstituted by identical or different substituents from the group consisting of fluorine, chlorine, $C_1$–$C_4$-alkyl, $C_1$–$C_4$-alkoxy, $C_1$–$C_2$-halogenoalkyl, $C_1$–$C_2$-halogenoalkoxy, nitro and cyano, or together particularly preferably represent $C_2$–$C_6$-alkanediyl which is optionally mono- to trisubstituted by identical or different substituents from the group consisting of fluorine, chlorine, $C_1$–$C_4$-alkyl, $C_1$–$C_4$-alkoxy and $C_1$–$C_2$-halogenoalkyl, and $R^{10}$ and $R^{11}$ independently of one another each particularly preferably represent $C_1$–$C_8$-alkyl, $C_2$–$C_8$-alkenyl, $C_1$–$C_8$-alkoxy, $C_1$–$C_8$-alkylamino, $C_3$–$C_8$-alkenylamino, di-($C_1$–$C_8$-alkyl)-amino or di-($C_3$–$C_8$-alkenyl)-amino, each of which is optionally mono- to pentasubstituted by identical or different substituents from the group consisting of fluorine and chlorine.

X very particularly preferably represents fluorine, chlorine, bromine, methyl, ethyl, propyl, isopropyl, ethenyl, 1-propenyl, methoxy, ethoxy, propoxy, isopropoxy, allyloxy, methallyloxy, trifluoromethyl, difluoromethoxy, trifluoromethoxy, trifluoroethoxy, methylthio, methylsulphinyl, methylsulphonyl, nitro, cyano, or very particularly preferably represents respectively optionally fluorine-, chlorine-, bromine-, methyl-, ethyl-, propyl-, isopropyl-, tert-butyl-, methoxy-, ethoxy-, propoxy-, tert-butoxy-, trifluoromethyl-, trifluoromethoxy-, nitro- or cyano-substituted phenyl, phenoxy, phenylthio, benzyloxy or benzylthio.

Y very particularly preferably represents hydrogen, fluorine, chlorine, bromine, methyl, ethyl, n-propyl, i-propyl, n-butyl, i-butyl, tert-butyl, ethenyl, 1-propenyl, methoxy, ethoxy, propoxy, isopropoxy, allyloxy, methallyloxy, trifluoromethyl, methylthio, methylsulphinyl, methylsulphonyl, difluoromethoxy, trifluoromethoxy, trifluoroethoxy, nitro or cyano.

Z very particularly preferably represents fluorine, chlorine, bromine, methyl, ethyl, n-propyl, i-propyl, n-butyl, i-butyl, tert-butyl, ethenyl, 1-propenyl, methoxy, ethoxy, propoxy, isopropoxy, allyloxy, methallyloxy, trifluoromethyl, difluoromethoxy, trifluoromethoxy, trifluoroethoxy, nitro or cyano.

A and Q together very particularly preferably represent $C_1$–$C_4$-alkanediyl or $C_2$–$C_4$-alkenediyl, each of which is optionally mono- or disubstituted by identical or different substituents from the group consisting of fluorine, chlorine, hydroxyl, and of $C_1$–$C_6$-alkyl and $C_1$–$C_2$-alkoxy, each of which is optionally mono- to trisubstituted by identical or different substituents from the group consisting of fluorine and chlorine.

B and B' independently of one another each very particularly preferably represent hydrogen, methyl or ethyl, G very particularly preferably represents hydrogen (a) or one of the groups

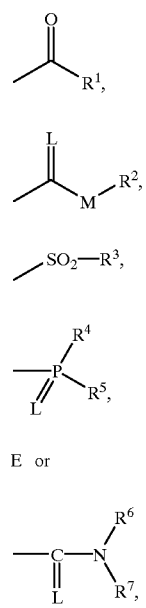

(b)

(c)

(d)

(e)

E or (f)

(g)

in which

E represents a metal ion equivalent or an ammonium ion,

L represents oxygen or sulphur and

M represents oxygen or sulphur, $R^1$ very particularly preferably represents $C_1$–$C_{14}$-alkyl, $C_2$–$C_6$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl, each of which is optionally mono- to pentasubstituted by identical or different substituents from the group consisting of fluorine and chlorine, or very particularly preferably represents $C_3$–$C_6$-cycloalkyl which is optionally mono- or disubstituted by identical or different substituents from the group consisting of fluorine, chlorine, methyl, ethyl, methoxy and ethoxy and in which one or two not directly adjacent methylene groups may be replaced by oxygen and/or sulphur atoms, very particularly preferably represents phenyl which is optionally mono- or disubstituted by identical or different substituents from the group consisting of fluorine, chlorine, bromine, methyl, ethyl, propyl, i-propyl, methoxy, ethoxy, trifluoromethyl, trifluoromethoxy, cyano and nitro, very particularly preferably represents benzyl which is optionally mono- or disubstituted by identical or different substituents from the group consisting of fluorine, chlorine, bromine, methyl, ethyl, propyl, i-propyl, methoxy, ethoxy, trifluoromethyl and trifluoromethoxy, very particularly preferably represents thienyl, furanyl or pyridyl, each of which is optionally mono- or disubstituted by identical or different substituents from the group consisting of fluorine, chlorine, bromine, methyl and ethyl, very particularly preferably represents phenoxy-$C_1$–$C_4$-alkyl which is optionally mono- or disubstituted by identical or different substituents from the group consisting of fluorine, chlorine, methyl and ethyl, or very particularly preferably represents pyridyloxy-$C_1$–$C_4$-alkyl, pyrimidyloxy-$C_1$–$C_4$-alkyl or thiazolyloxy-$C_1$–$C_4$-alkyl, each of which is optionally mono- or disubstituted by identical or different substituents from the group consisting of fluorine, chlorine, amino, methyl and ethyl.

$R^2$ very particularly preferably represents $C_1$–$C_{14}$-alkyl, $C_2$–$C_6$-alkenyl, $C_1$–$C_4$-alkoxy-$C_2$–$C_6$-alkyl or poly-$C_1$–$C_4$-alkoxy-$C_2$–$C_6$-alkyl, each of which is optionally mono- to pentasubstituted by identical or different substituents from the group consisting of fluorine and chlorine, very particularly preferably represents $C_3$–$C_6$-cycloalkyl which is optionally mono- to trisubstituted by identical or different substituents from the group consisting of fluorine, chlorine, methyl, ethyl, methoxy and ethoxy, or very particularly preferably represents phenyl or benzyl, each of which is optionally mono- or disubstituted by identical or different substituents from the group consisting of fluorine, chlorine, nitro, cyano, methyl, ethyl, propyl, i-propyl, methoxy, ethoxy, trifluoromethoxy and trifluoromethyl.

$R^3$ very particularly preferably represents $C_1$–$C_6$-alkyl, which is optionally mono- to trisubstituted by identical or different substituents from the group consisting of fluorine and chlorine, or very particularly preferably represents phenyl or benzyl, each of which is optionally mono- or disubstituted by fluorine, chlorine, bromine, methyl, ethyl, methoxy, ethoxy, trifluoromethyl, trifluoromethoxy, cyano or nitro.

$R^4$ and $R^5$ independently of one another each very particularly preferably represent $C_1$–$C_4$-alkyl, $C_1$–$C_4$-alkoxy, $C_1$–$C_4$-alkylamino, di-($C_1$–$C_4$-alkyl)-amino, $C_1$–$C_4$-alkylthio, each of which is optionally mono- to trisubstituted by identical or different substituents from the group consisting of fluorine and chlorine, or very particularly preferably represents phenyl, phenoxy or phenylthio, each of which is optionally mono- or disubstituted by identical or different substituents from the group consisting of fluorine, chlorine, bromine, nitro, cyano, $C_1$–$C_2$-alkoxy, trifluoromethoxy, $C_1$–$C_2$-alkylthio, trifluoromethyl or $C_1$–$C_3$-alkyl.

$R^6$ very particularly preferably represents hydrogen, very particularly preferably represents $C_1$–$C_6$-alkyl, $C_1$–$C_6$-alkoxy-$C_2$–$C_4$-alkyl, each of which is optionally monoto trisubstituted by identical or different substituents from the group consisting of fluorine and chlorine, very particularly preferably represents $C_3$–$C_6$-cycloalkyl which is optionally mono- or disubstituted by identical or different substituents from the group consisting of fluorine, chlorine, methyl, methoxy, trifluoromethyl and trifluoromethoxy, very particularly preferably represents phenyl which is optionally mono- or disubstituted by identical or different substituents from the group consisting of fluorine, chlorine, trifluoromethyl, $C_1$–$C_4$-alkyl, trifluoromethoxy and $C_1$–$C_4$-alkoxy, or very particularly preferably represents benzyl which is optionally mono- or disubstituted by identical or different substituents from the group consisting of fluorine, chlorine, $C_1$–$C_4$-alkyl, trifluoromethyl, trifluoromethoxy and $C_1$–$C_4$-alkoxy.

$R^7$ very particularly preferably represents hydrogen, or very particularly preferably represents $C_1$–$C_6$-alkyl or $C_3$–$C_6$-alkenyl, each of which is optionally mono- to trisubstituted by identical or different substituents from the group consisting of fluorine and chlorine, or $R^6$ and $R^7$ very particularly preferably combine with the linking N-atom to form an optionally oxygen- or sulphur-containing, optionally methyl-substituted 5- to 7-membered ring.

In each case, X, Y and Z may not simultaneously represent methyl.

The abovementioned definitions or illustrations of radicals mentioned generally or in preferred ranges can be combined with each other as desired, i.e. including combinations between the respective ranges and preferred ranges. They apply both to the end products and, correspondingly, to the precursors and intermediates.

In the abovementioned definitions, saturated or unsaturated hydrocarbon radicals can in each case, as far as possible, be straight-chain or branched, i.e. including in combination with hetero atoms (for example alkoxy or alkenylthio).

According to the invention, preference is given to compounds of the formula (I) in which there exists a combination of the meanings mentioned above as preferred (preferable).

According to the invention, particular preference is given to compounds of the formula (I) in which there exists a combination of the meanings mentioned above as particularly preferred.

According to the invention, very particular preference is given to the compounds of the formula (I) in which there exists a combination of the meanings mentioned above as very particularly preferred.

Unless otherwise specified, substituted radicals may be mono- or polysubstituted by identical or different possible substituents.

In addition to the compounds mentioned in the Preparation Examples, the following 2-phenyl-substituted 3-hydroxy-$\Delta^2$-cyclopentenone derivatives of the formula (Ia) may be specifically mentioned:

TABLE 1

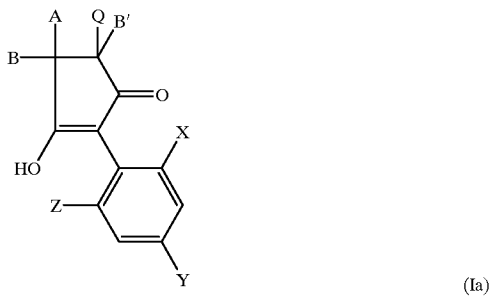

(Ia)

| A Q | B | B' | X | Y | Z |
|---|---|---|---|---|---|
| —$CH_2$— | H | H | Br | $CH_3$ | $CH_3$ |
| —$(CH_2)_2$— | H | H | Br | $CH_3$ | $CH_3$ |
| —CH—CH— $\quad\quad\;$\| $\quad\;$\| $\quad\;$ $CH_3$ $CH_3$ | H | H | Br | $CH_3$ | $CH_3$ |
| —$(CH_2)_2$— | $CH_3$ | $CH_3$ | Br | $CH_3$ | $CH_3$ |
| —$(CH_2)_3$— | H | H | Br | $CH_3$ | $CH_3$ |
| —$(CH_2)_2$—$CHCH_3$— | H | H | Br | $CH_3$ | $CH_3$ |
| —$(CH_2)_2$—$CHOCH_3$— | H | H | Br | $CH_3$ | $CH_3$ |
| —$CH_2$—$CHCH_3$—$CH_2$— | H | H | Br | $CH_3$ | $CH_3$ |
| —$CH_2$—$CHOCH_3$—$CH_2$— | H | H | Br | $CH_3$ | $CH_3$ |
| —$CH_2$—$CHCH_3$—$CHCH_3$— | H | H | Br | $CH_3$ | $CH_3$ |
| —$CH_2$—$CHOCH_3$—$CHOCH_3$— | H | H | Br | $CH_3$ | $CH_3$ |
| —$(CH_2)_4$— | H | H | Br | $CH_3$ | $CH_3$ |
| —$(CH_2)_3$—$CHCH_3$— | H | H | Br | $CH_3$ | $CH_3$ |
| —$(CH_2)_3$—$CHOCH_3$— | H | H | Br | $CH_3$ | $CH_3$ |
| —$(CH_2)_2$—$CHCH_3$—$CH_2$ | H | H | Br | $CH_3$ | $CH_3$ |
| —$(CH_2)_2$—$CHOCH_3$—$CH_2$— | H | H | Br | $CH_3$ | $CH_3$ |
| —$(CH_2)_3$—$CHCH_3$— | H | H | Br | $CH_3$ | $CH_3$ |
| —$(CH_2)_3$—$CHOCH_3$— | H | H | Br | $CH_3$ | $CH_3$ |
| —$(CH_2)_4$— | $CH_3$ | H | Br | $CH_3$ | $CH_3$ |
| —$CH_2$—$CHCH_3$—$CHCH_3$—$CH_2$— | H | H | Br | $CH_3$ | $CH_3$ |

TABLE 1-continued (Structure Ia shown with substituents A, Q, B, B', X, Y, Z on cyclopentanone-phenyl scaffold)

| A | Q | B | B' | X | Y | Z |
|---|---|---|---|---|---|---|
| —(CH$_2$)$_2$—CHCH$_3$—CHCH$_3$— | | H | H | Br | CH$_3$ | CH$_3$ |
| —(CH$_2$)$_2$—CHOH—CH$_2$— | | H | H | Br | CH$_3$ | CH$_3$ |
| —CH$_2$—CHOH—CHOH—CH$_2$— | | H | H | Br | CH$_3$ | CH$_3$ |
| —CH$_2$—CH(—O—CH$_2$—O—)CH—CH$_2$— | | H | H | Br | CH$_3$ | CH$_3$ |
| —CH$_2$—CH(—O—C(CH$_3$)$_2$—O—)CH—CH$_2$— | | H | H | Br | CH$_3$ | CH$_3$ |
| —(CH$_2$)$_4$— | | | | —CH$_2$— | Br | CH$_3$ | CH$_3$ |
| —(CH$_2$)$_4$— | | | | —(CH$_2$)$_2$— | Br | CH$_3$ | CH$_3$ |
| —(CH$_2$)$_2$—C(=O)—CH$_2$— | | H | H | Br | CH$_3$ | CH$_3$ |
| —(CH$_2$)$_2$—C(=N—OCH$_3$)—CH$_2$— | | H | H | Br | CH$_3$ | CH$_3$ |

Table 2
  A, Q, B and B' are each as defined in Table 1
  X=CH$_3$ Y=Br Z=CH$_3$
Table 3
  A, Q, B and B' are each as defined in Table 1
  X=C$_2$H$_5$ Y=Br Z=CH$_3$
Table 4
  A, Q, B and B' are each as defined in Table 1
  X=Cl Y=CH$_3$ Z=CH$_3$
Table 5
  A, Q, B and B' are each as defined in Table 1
  X=CH$_3$ Y=Cl Z=CH$_3$
Table 6
  A, Q, B and B' are each as defined in Table 1
  X=OCH$_3$ Y=CH$_3$ Z=CH$_3$
Table 7
  A, Q, B and B' are each as defined in Table 1
  X=CH$_3$ Y=OCH$_3$ Z=CH$_3$
Table 8
  A, Q, B and B' are each as defined in Table 1
  X=OCH$_3$ Y=H Z=CH$_3$
Table 9
  A, Q, B and B' are each as defined in Table 1
  X=Cl Y=H Z=CH$_3$
Table 10
  A, Q, B and B' are each as defined in Table 1
  X=Cl Y=H Z=Cl
Table 11
  A, Q, B and B' are each as defined in Table 1
  X=CH$_3$ Y=H Z=CH$_3$
Table 12
  A, Q, B and B' are each as defined in Table 1
  X=Cl Y=Cl Z=CH$_3$
Table 13
  A, Q, B and B' are each as defined in Table 1
  X=Cl Y=CH$_3$ Z=Cl
Table 14
  A, Q, B and B' are each as defined in Table 1
  X=Cl Y=H Z=OCH$_3$
Table 15
  A, Q, B and B' are each as defined in Table 1
  X=CH$_3$ Y=CN Z CH$_3$
Table 16
  A, Q, B and B' are each as defined in Table 1
  X=CN Y=CH$_3$ Z=CH$_3$ If according to process (A) ethyl 5-(2-chloro-6-methylphenyl)-2,3-tetramethylene-4-oxo-valerate is used, the course of the process according to the invention can be represented by the following equation:

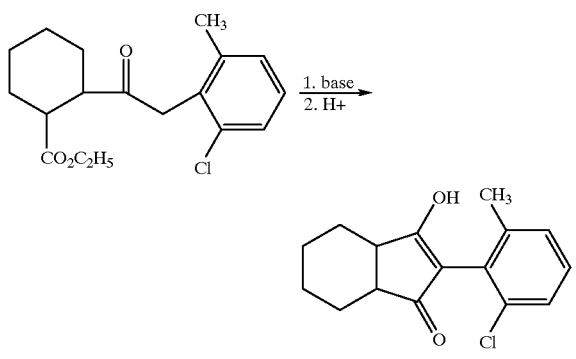

If according to process (B) (variant α) 2-(2,4-dichloro-6-methylphenyl)4,5-(2,3-dimethyl)-tetramethylene-3-hydroxy-2-cyclopentene-1-one and pivaloyl chloride are used as starting materials, the course of the process according to the invention can be represented by the following equation:

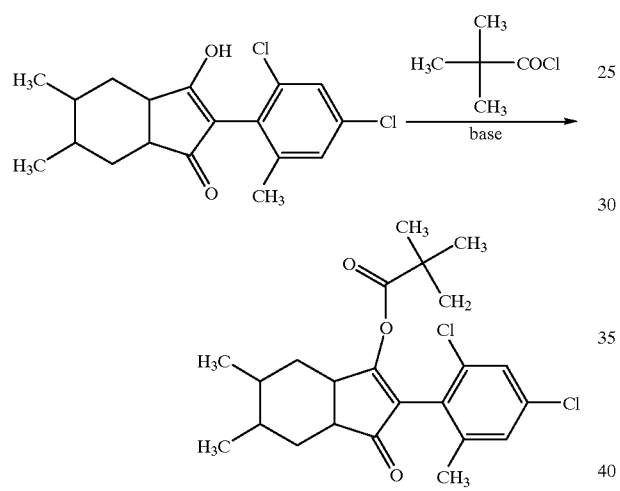

If according to process B (variant β) 2-(2-chloro-6-methoxyphenyl)4,5-methylene-3-hydroxy-2-cyclopentene-1-one and acetic anhydride are used as starting materials, the course of the process according to the invention can be represented by the following equation:

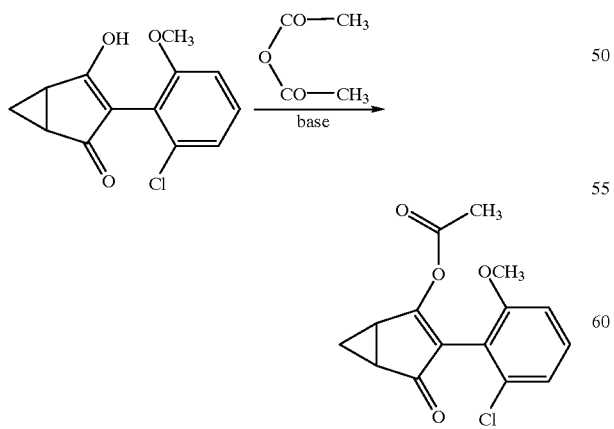

If according to process (C) 2-(2-chloro-4,6-dimethylphenyl)4,5-(3-oxo)-tetramethylene-3-hydroxy-2-cyclopentene-1-one and ethoxyethyl chloroformate are used as starting compounds, the course of the process according to the invention can be represented by the following equation.

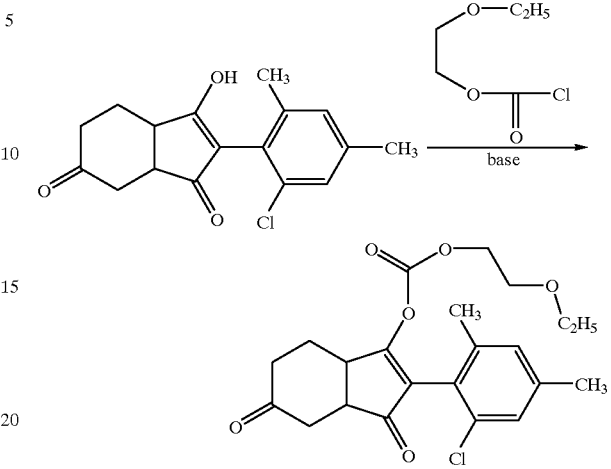

If according to process (D$_\alpha$) 2-(4-chloro-2,6-dimethylphenyl)-4,5-(3-methyl)-tetramethylene-3-hydroxy-2-cyclopentene-1-one and methyl chloromonothioformate are used as starting materials, the course of the reaction can be represented in the following manner:

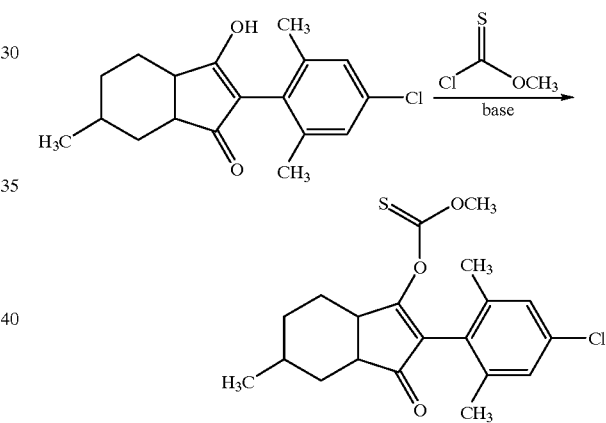

If according to process (D$_\beta$) 2-(2,6-dichlorophenyl)4,5-trimethylene-3-hydroxy-2-cyclopentene-1-one, carbon disulphide and methyl iodide are used as starting materials, the course of the reaction can be represented as follows:

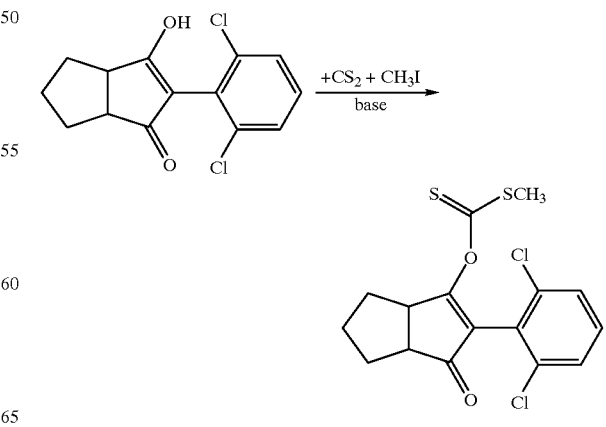

If according to process (E) 2-(4-bromo-2,6-dimethylphenyl)-4,5-(3-methoxy)-tetramethylene-3- hydroxy-2-cyclopentene-1-one and methanesulphonyl chloride are used as starting material, the course of the reaction can be represented by the following equation:

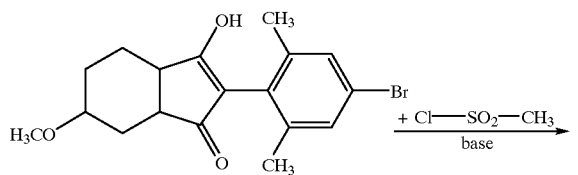

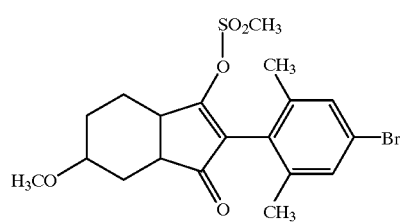

If according to process (F) 2-(4-bromo-2,6-dimethylphenyl-4,5-(4-methyl)-tetramethylene-3-hydroxy-2-cyclopentene-1-one and 2,2,2-trifluoroethyl chloromethanethiophosphonate are used as starting materials, the course of the reaction can be represented by the following equation:

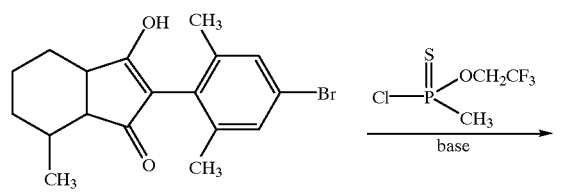

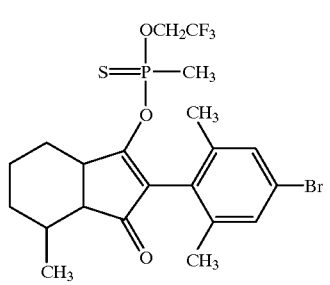

If according to process (G) 2-(2-bromo-4,6-dimethylphenyl)4,5-(3,3-ethylenedioxy)-tetramethylene-3-hydroxy-2-cyclopentene-1-one and NaOH are used as components, the course of the process according to the invention can be represented by the following equation:

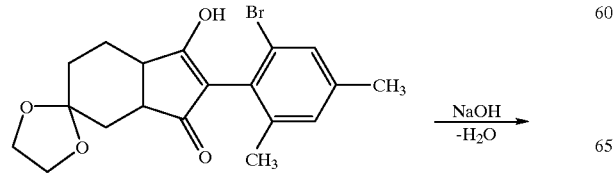

-continued

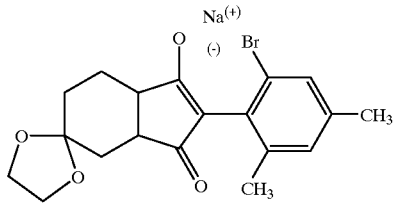

If according to process ($H_\alpha$) 2-(2-methoxy-4,6-dimethylphenyl)-4,5-(3-methoxy)-tetramethylene-3-hydroxy-2-cyclopentene-1-one and ethyl isocyanate are used as starting materials, the course of the reaction can be represented by the following scheme:

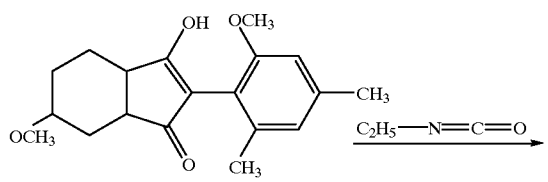

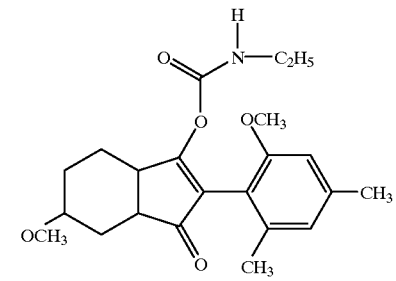

If according to process ($H_\beta$) 2-(4-methoxy-2,6-dimethylphenyl)4,5-tetramethylene-3-hydroxy-2-cyclopentene-1-one and dimethylcarbamoyl chloride are used as starting materials, the course of the reaction can be represented by the following scheme:

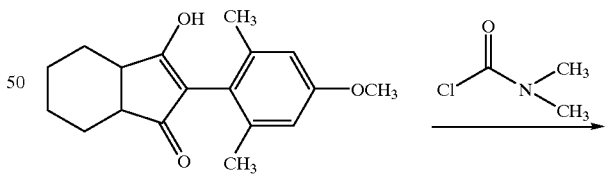

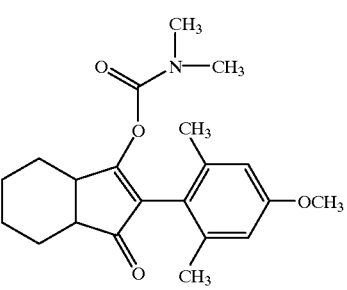

The compounds of the formula (II)

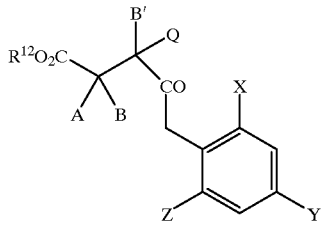
(II)

in which
A, B, B', Q, X, Y, Z and $R^{12}$ are each as defined above required as starting materials in process (A) above are novel. They can be prepared by methods which are known in principle. The 5-aryl-4-ketocarboxylic esters of the formula (II) are obtained, for example, when 5-aryl-4-ketocarboxylic acids of the formula (XIV)

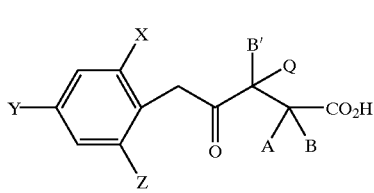
(XIV)

in which
A, B, B', Q, X, Y and Z are each as defined above are esterified (cf. for example Organikum, 15th edition, Berlin, 1977, page 499).

The 5-aryl-4-ketocarboxylic acids of the formula (XIV)

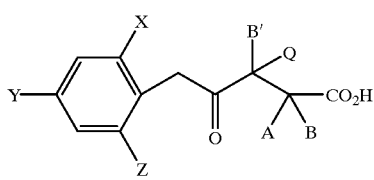
(XIV)

in which
A, B, B', Q, X, Y and Z are each as defined above are novel; however, they can be prepared by methods which are known in principle.

The 5-aryl-4-ketocarboxylic acids of the formula (XIV) are obtained, for example, when carboxylic anhydrides of the formula (XV)

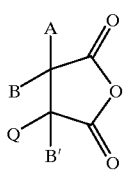
(XV)

in which
A, B, B' and Q are each as defined above are reacted with organometallic compounds of the formula (XVI)

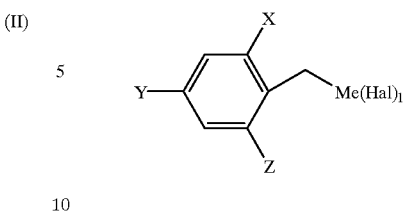
(XVI)

in which
X, Y and Z are each as defined above,

Me represents mono- or bivalent metal ions (for example of lithium or magnesium), Hal represents chlorine or bromine and I represents a number 0 or 1, in the presence of a diluent (cf. for example Organikum, 15th edition, Berlin, 1977, page 623).

Some of the compounds (XV) and (XVI) are known and/or they can be prepared in a simple manner by known processes (cf. for example Organikum, 15th edition, Berlin, 1977, pages 525, 526 and 623).

Additionally, 5-aryl4-ketocarboxylic acids of the formula (XIV)

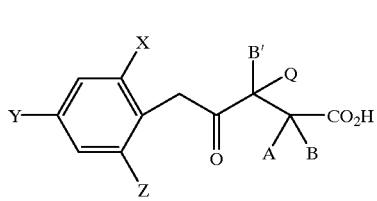
(XIV)

in which

A, B, B', Q, X, Y and Z are each as defined above are obtained when substituted 2-phenyl-3-oxo-adipic esters of the formula (XVII)

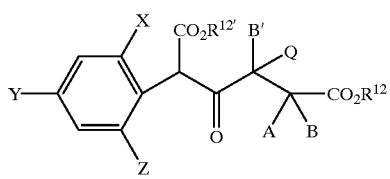
(XVII)

in which

A, B, B', Q, X, Y and Z are each as defined above and $R^{12}$ and $R^{12'}$ each represent alkyl (preferably $C_1$–$C_6$-alkyl) are decarboxylated, if appropriate in the presence of a diluent and if appropriate in the presence of a base or an acid (cf. for example Organikum, 15th edition, Berlin, 1977, pages 519 to 521).

The compounds of formula (XVII)

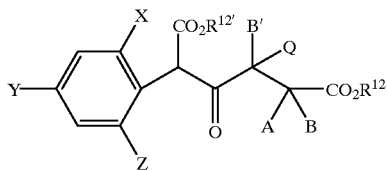

in which

A, B, B', Q, X, Y, Z, $R^{12}$ and $R^{12'}$ are each as defined above
are novel and obtainable
when dicarboxylic monoester chlorides of the formula (XVIII)

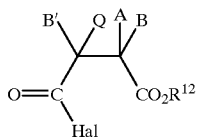

in which

A, B, B', Q and $R^{12}$ are each as defined above and
Hal represents chlorine or bromine
or carboxylic anhydrides of the formula (XV)

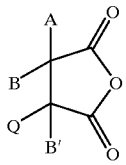

in which

A, B, B' and Q are each as defined above
are acylated with a substituted phenylacetate of the formula (XIX)

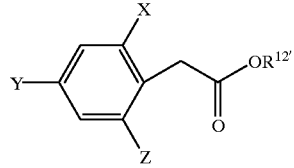

in which

X, Y, Z and $R^{12'}$ are each as defined above,
in the presence of a diluent and in the presence of a base (cf. for example M. S. Chambers, E. J. Thomas, D. J. Williams, J. Chem. Soc. Chem. Commun., (1987), 1228).

Some of the compounds of formula (XVIII) and (XIX) are known and/or they can be prepared by known processes.

In each case, the active compounds of the formulae (Ib) to (Ig) according to the invention are prepared starting from the compounds of the formula (Ia) obtainable by process (A) according to the invention. They are important intermediates for preparing the compounds of the formulae (Ib) to (Ig).

The acyl halides of the formula (III), carboxylic anhydrides of the formula (IV), chloroformic acid esters or chloroformic acid thioesters of formula (V), chloromonothioformic acid esters or chlorodithioformic acid esters of the formula (VI), alkyl halides of the formula (VII), sulphonyl chlorides of the formula (VIII), phosphorus compounds of the formula (IX) and metal compounds or amines of the formulae (X) and (XI) and isocyanates of the formula (XII) and carbamoyl chlorides or thiocarbamoyl chlorides of the formula (XIII) additionally required as starting materials for carrying out the compounds (B), (C), (D), (E), (F), (G) and (H) according to the invention are generally known compounds of organic or inorganic chemistry.

The process (A) is characterized in that compounds of the formula (II), in which A, B, B', Q, X, Y, Z and $R^{12}$ are each as defined above, are subjected to an intramolecular condensation in the presence of bases.

Suitable diluents for the process (A) according to the invention are all organic solvents which are inert to the reaction participant. Those preferably utilizable are hydrocarbons, such as toluene and xylene, furthermore ethers, such as dibutyl ether, tetrahydrofuran, dioxane, glycol dimethyl ether and diglycol dimethyl ether, additionally polar solvents, such as dimethyl sulphoxide, sulpholane, dimethylformamide and N-methyl-pyrrolidone. Furthermore, it is possible to use alcohols such as methanol, ethanol, propanol, iso-propanol, butanol, isobutanol, tert-butanol.

Suitable bases (deprotonating agents) for carrying out process (A) according to the invention are all customary proton acceptors.

Those preferably utilizable are alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (methyltrialkyl($C_8$–$C_8$)ammonium chloride) or TDA 1 (tris-(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed. When carrying out process (A) according to the invention, the reaction temperatures can be varied within a relatively wide range. In general, the reaction is carried out at temperatures between 0° C. and 250° C., preferably between 50° C. and 150° C.

The process (A) according to the invention is generally carried out under atmospheric pressure.

When carrying out process (A) according to the invention, the reaction components of the formula (II) and the deprotonating bases are generally employed in approximately equimolar amounts. However, it is also possible to use one component or the other in a relatively large excess (up to 3 mol).

Process (Bα) is characterized in that compounds of the formula (Ia) are reacted with carboxylic acid halides of the formula (III).

Suitable diluents for the process (Bα) according to the invention are all solvents which are inert to the acyl halides. Those preferably utilizable are hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, and moreover carboxylic esters, such as ethyl acetate, and also strongly polar solvents, such as dimethyl sulphoxide and sulpholane. The hydrolytic stability of the acyl halide permitting, the reaction can also be carried out in the presence of water.

Suitable acid binders for the reaction according to process (Bα) according to the invention are all customary acid acceptors. Preferably utilizable are tertiary amines, such as triethylamine, pyridine, diazabicyclooctane (DABCO), diazabicycloundecane (DBU), diazabicyclononene (DBN), Hünig base and N,N-dimethyl-aniline, furthermore alkaline earth metal oxides, such as magnesium oxide and calcium oxide, and additionally alkali metal carbonates and alkaline earth metal carbonates, such as sodium carbonate, potassium carbonate and calcium carbonate.

In the process (Bα) according to the invention, the reaction temperatures can be varied within a relative wide range. In general, the reaction is carried out at temperatures of between −20° C. and +150° C., preferably between 0° C. and 100° C.

When carrying out the process (Bα) according to the invention, the starting materials of the formula (Ia) and the carboxylic acid halide of the formula (III) are generally employed in approximately equimolar amounts. However, it is also possible to use a relatively large excess (up to 5 mol) of the carboxylic acid halide. Work-up is carried out by customary methods.

The process (Bβ) is characterized in that compounds of the formula (Ia) are reacted with carboxylic anhydrides of the formula (IV).

Diluents which are preferred for use in the process (Bβ) according to the invention are those diluents which are also preferred when acyl halides are employed. Furthermore, a carboxylic anhydride employed in excess can furthermore act as diluent.

In the process (Bβ) according to the invention, the reaction temperatures can be varied within a relatively wide range. In general, the reaction is carried out at temperatures of between −20° C. and +150° C., preferably between 0° C. and 100° C.

When carrying out the process (Bβ) according to the invention, the starting materials of the formula (Ia) and the carboxylic anhydride of the formula (IV) are generally employed in approximately equivalent amounts. However, it is also possible to employ the carboxylic anhydride in a relatively large excess (up to 5 mol). Work-up is carried out by customary methods.

In general, a procedure is used in which diluent and excess carboxylic anhydride and the resulting carboxylic acid are removed by distillation or by washing with an organic solvent or with water.

The process (C) is characterized in that compounds of the formula (Ia) are reacted with chloroformic acid esters or chloroformic acid thioesters of the formula (V).

Suitable acid binders for the reaction by the process (C) according to the invention are all customary acid acceptors. Those preferably utilizable are tertiary amines, such as triethylamine, pyridine, DABCO, DBU, DBN, Hünig base and N,N-dimethylanilin, furthermore alkaline earth metal oxides, such as magnesium oxide and calcium oxide, additionally alkali metal and alkaline earth metal carbonates, such as sodium carbonate, potassium carbonate and calcium carbonate.

Suitable diluents for the process (C) according to the invention are all solvents which are inert to the starting materials. Those preferably utilizable are hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, methyl tert-butyl ether tetrahydrofuran and dioxane, moreover carboxylic acid esters, such as ethyl acetate, and also strongly polar solvents, such as dimethyl sulphoxide and sulpholane.

When carrying out process (C) according to the invention, the reaction temperatures can be varied within a relatively wide range. If the reaction is carried out in the presence of a diluent and an acid binder, the reaction temperatures are generally between −20° C. and +100° C., preferably between 0° C. and 50° C.

Process (C) according to the invention is generally carried out under atmospheric pressure.

When carrying out the process (C) according to the invention, the starting materials of the formula (Ia) and the corresponding chloroformic acid esters or chloroformic acid thioesters of the formula (V) are generally employed in approximately equivalent amounts. However, it is also possible to employ one component or the other in a relatively large excess (up to 2 mol). Work-up is then carried out by customary methods. In general, a procedure is used in which precipitated salts are removed and the reaction mixture which remains is concentrated by stripping off the diluent.

In the preparation process (Dα), about 1 mol of chloromonothioformic acid ester or chlorodithioformic acid ester of the formula (VI) is reacted per mole of starting material of the formula (Ia) at 0 to 120° C., preferably at 20 to 60° C. Diluents which may be added, if appropriate, are all inert organic solvents, such as halogenated hydrocarbons, ethers, amides, alcohols, nitriles, sulphones and sulphoxides.

Preference is given to using acetonitrile, dimethyl sulphoxide, methyl tert-butyl ether, tetrahydrofuran, dimethylformamide, ethyl acetate or methylene chloride.

If, in a preferred embodiment, the enolate salt of the compound of the formula (Ia) is prepared by addition of strong deprotonating agents such as, for example, sodium hydride and potassium tertiary-butoxide, the further addition of acid binders can be dispensed with.

If acid binders are used, customary inorganic or organic bases are suitable. Sodium hydroxide, sodium carbonate, potassium carbonate, pyridine and triethylamine may be mentioned by way of example.

The reaction can be carried out under atmospheric pressure or under elevated pressure. It is preferably carried out under atmospheric pressure. Work-up is carried out according to customary methods.

In preparation process (Dβ), the equimolar amount or an excess of carbon disulphide is added per mole of the starting material of the formula (II). Here, the reaction is preferably carried out at temperatures from 0 to 50° C., and in particular at 20 to 30° C.

Suitable bases for process (Dβ) are all customary proton acceptors. Those preferably utilizable are alkali metal hydrides, alkali metal alkoxides, alkali metal or alkaline earth metal carbonates or bicarbonates or nitrogen bases. Examples include sodium hydride, sodium methoxide, sodium hydroxide, calcium hydroxide, potassium carbonate, sodium dicarbonate, triethylamine, dibenzylamine, diisopropylamine, pyridine, quinoline, diazabicyclooctane (DABCO), diazabicyclononene (DBN) and diazabicycloundecene (DBU).

Suitable for use as diluents in this process are all customary solvents.

Those preferably utilizable are aromatic hydrocarbons, such as benzene or toluene, alcohols, such as methanol, ethanol, isopropanol or ethylene glycol, nitriles, such as acetonitrile, ethers, such as tetrahydrofuran or dioxane, amides, such as dimethylformamide, or other polar solvents, such as dimethyl sulphoxide or sulpholane.

In many cases, it is advantageous to initially prepare corresponding salt from the compound of the formula (Ia) by addition of a deprotonating agent (such as, for example, potassium tertiary-butoxide or sodium hydride). The compound of the formula (Ia) is reacted with carbon disulphide until the formation of the intermediate has ended, for example after stirring at room temperature for several hours.

The further reaction with the alkyl halide of the formula (VII) is preferably carried out at 0 to 70° C. and in particular at 20 to 50° C. At least the equimolar amount of alkyl halide is employed.

The reaction is carried out under atmospheric pressure or under elevated pressure, preferably under atmospheric pressure.

Once again, work-up is carried out by customary methods.

In preparation process (E), about 1 mole of sulphonyl chloride of the formula (III) is employed per mole of starting material of the formula (Ia), at 0 to 150° C., preferably at 20 to 70° C.

Diluents which may be added, if appropriate, are all inert organic solvents, such as halogenated hydrocarbons, ethers, amides, carboxylic esters, nitriles, sulphones or sulphoxides.

Preference is given to using acetonitrile, dimethylsulphoxide, ethyl acetate, methyl tert-butyl ether, tetrahydrofuran, dimethylformamide or methylene chloride.

If, in a preferred embodiment, the enolate salt of the compound of the formula (Ia) is prepared by addition of strong deprotonating agents (such as, for example, sodium hydride or potassium tert-butoxide), the further addition of acid-binder can be dispensed with.

If acid-binders are used, customary inorganic or organic bases are suitable. Sodium hydroxide, sodium carbonate, potassium carbonate and pyridine may be mentioned by way of example.

The reaction can be carried out under atmospheric pressure or under elevated pressure. It is preferably carried out under atmospheric pressure. Work-up is carried out according to customary methods.

If appropriate, preparation process (E) can be carried out under phase-transfer conditions (W. J. Spillane et. al.; J. Chem. Soc., Perkin Trans I, (3) 677–9 (1982)). In this case, 0.3 to 5 mol of sulphonyl chloride of the formula (VIII), preferably 1 mol, is employed per mole of starting material of the formula (Ia), at 0° to 150° C., preferably at 20 to 70° C.

Suitable phase-transfer catalysts are all quaternary ammonium salts, preferably tetraoctylammonium bromide and benzyltriethylammonium chloride. In this case, all nonpolar inert solvents may serve as organic solvent, preference is given to using benzene or toluene.

In preparation process (F), 1 to 2, preferably 1 to 1.3 mol of the phosphorus compound of the formula (IX) is employed per mol of compound of the formula (Ia), at temperatures between –40° C. and 150° C., preferably between –10 and 100° C., to obtain compounds of the formula (Ie).

Diluents which may be added, if appropriate, are all inert organic solvents such as halogenated hydrocarbons, ethers, amides, nitriles, carboxylic esters, sulphones, sulphoxides, etc.

Preference is given to using acetonitrile, dimethyl sulphoxide, ethyl acetate, methyl tert-butyl ether, tetrahydrofuran, dimethylformamide or methylene chloride.

Acid binders which may be added, if appropriate, are all customary inorganic or organic bases, such as hydroxides, amides, carbonates. Examples include sodium hydroxide, sodium carbonate, potassium carbonate, pyridine, triethylamine or DABCO.

The reaction can be carried out under atmospheric pressure or under elevated pressure, it is preferably carried out under atmospheric pressure. Work-up takes place according to customary methods of organic chemistry. The resulting end products are preferably purified by crystallization, chromatographic purification or by so-called "incipient distillation", i.e. removal of the volatile constituents under reduced pressure.

The process (G) is characterized in that compounds of the formula (Ia) are reacted with metal compounds of the formula (X) or amines of the formula (XI).

Preferred diluents for the process according to the invention are ethers, such as tetrahydrofuran, dioxane, diethyl ether, or else alcohols, such as methanol, ethanol, isopropanol, but also water. The process (G) according to the invention is generally carried out under atmospheric pressure. The reaction temperatures are generally between –20° C. and 100° C., preferably between 0° C. and 50° C.

When carrying out the process (H) according to the invention, the starting materials of the formulae (Ia) and (XII) or (XIII) are generally employed in approximately equimolar amounts. However, it is also possible to use one or the other component in a relatively large excess (up to 2 mol). In general, a procedure is used in which the reaction mixture is concentrated by stripping off the diluent.

In preparation process (Hα), about 1 mol of isocyanate or isothiocyanate of the formula (XII) is employed per mole of starting material of the formula (Ia), at 0 to 100° C., preferably at 20 to 50° C.

Diluents which may be added, if appropriate, are all inert organic solvents, such as hydrocarbons, halogenated hydrocarbons, ethers, carboxylic esters, amides, nitriles, sulphones, sulphoxides.

Preference is given to using toluene, methylene chloride, tetrahydrofuran, ethyl acetate, dimethylformamide or dimethyl sulphoxide.

If appropriate, catalysts may be added to accelerate the reaction. Catalysts which can be employed very advantageously are organotin compounds, such as, for example, dibutyltin dilaurate.

The reaction is preferably carried out under atmospheric pressure.

In preparation process (Hβ), about 1 mol of carbamoyl chloride or thiocarbamoyl chloride of the formula (XIII) is employed per mole of starting material of the formula (Ia), at 0 to 150° C., preferably at 20 to 70° C.

Diluents which may be added, if appropriate, are all inert polar organic solvents, such as halogenated hydrocarbons, carboxylic esters, ethers, amides, nitriles, sulphones or sulphoxides.

Preference is given to using acetonitrile, ethyl acetate, dimethyl sulphoxide, methyl tert-butyl ether, tetrahydrofuran, dimethylformamide or methylene chloride.

If, in a preferred embodiment, the enolate salt of the compound of the formula (Ia) is prepared by addition of strong deprotonating agents (such as, for example, sodium hydride or potassium tertiary-butoxide), the further addition of acid binders can be dispensed with.

If acid binders are used, customary inorganic or organic bases are suitable. Sodium hydroxide or sodium carbonate, potassium carbonate, pyridine, triethylamine and DABCO may be mentioned by way of example.

The reaction can be carried out under atmospheric pressure or under elevated pressure, preferably under atmospheric pressure. Work-up takes place according to customary methods.

The active compounds are suitable for controlling animal pests, in particular insects, arachnids and nematodes which are encountered in agriculture, in forestry, in the protection of stored products and of materials, and in the hygiene sector. They are preferably employed as crop protection agents. They are active against normally sensitive and resistant species and against all or some stages of development. The abovementioned pests include:

From the order of the Isopoda, for example, Oniscus asellus, Armadillidium vulgare and Porcellio scaber.

From the order of the Diplopoda, for example, *Blaniulus guttulatus*.

From the order of the Chilopoda, for example, *Geophilus carpophagus* and Scutigera spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blatella germanica, Acheta domesticus*, Gryllotalpa spp., *Locusta migratoria migratorioides, Melanoplus differentialis* and *Schistocerca gregaria*.

From the order of the Dermaptera, for example, Forficula auricularia.

From the order of the Isoptera, for example, Reticulitermes spp.

From the order of the Anoplura, for example, *Pediculus humanus corporis, Haematopinus spp. and Linognathus spp.*

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Euryga ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretelia, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypodenna spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Mel oidogyne spp., Aphelenchoides spp., Longidorus spp., Xiphinema spp. and Trichodorus spp.

In particular, the compounds of the formula (I) according to the invention have excellent insecticidal activity. They have strong activity for example against the larvae of the mustard beetle (*Phaedon cochleariae*) and caterpillars of the cabbage moth (*Plutella maculipennis*).

The active compounds according to the invention can be used as defoliants, desiccants, haulm-killers and, especially, as weed-killers. By weeds, in the broadest sense, are to be understood all plants which grow in locations where they are unwanted. Whether the substances according to the invention act as total or selective herbicides depends essentially on the amount used.

The active compounds according to the invention can be used, for example, in connect ion with the following plants: Dicotyledonous weeds of the genera:

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicolyledonous crops of the genera:

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera:

Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbrist yl is, Sagittaria, Eleocharis, Scirpus, Paspalum, Ischaemum, Sphenoclea, Dactyloctenium, Agrostis, Alopecurus and Apera.

Monocotiledonous crops of the genera:

Oryza, Zea, Triticum, Hordeum, Avena, Secale, S orghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The active compounds according to the invention are highly suitable for the selective control of monocotyledonous weeds in dicotyledenous crops by both the pre- and the post-emergence method. They can be employed very successfully for controlling harmful grasses for example in cotton or sugar beet.

The active compounds can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates, suitable solid carriers for granules are: for example crushed and fractionated natural rocks such as calcite, marble, pumice, sepiolite and dolomite and synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids such as cephalins and lecithins, and synthetic phospholipids, can be used in the formulations. Possible further additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms prepared from these formulations, as a mixture with other active compounds, such as insecticides, attractants, sterilizing agents , bactericides, acaricides, nematicides, fungicides, growth-regulating substances or herbicides. The insecticides include, for example, phosphates, carbamates, carboxylates, chlorinated hydrocarbons, phenylureas and substances produced by micro organisms.

Examples of particularly advantageous mixture components are the following compounds:

Fungicides 2-aminobutane; 2-anilino-4-methyl-6-cyclopropyl-pyrimidine; 2',6'-dibromo-2-methyl-4'-trifluoromethoxyl-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozoinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebucanozole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin.

Bacillus thuringiensis, bendiocarb, benfuracarb, bensultap, beta-cyluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulphotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides for example anilides such as, for example, diflufenican and propanil; arylcarboxylic acids such as, for example, dichloropicolinic acid, dicamba and picloram; aryloxy-alkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenz-thiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulphuron, bensulphuron-methyl, chlorimuron-ethyl, chlorsulphuron, cinosulphuron, metsulphuron-methyl, nicosulphuron, primisulphuron, pyrazosulphuron-ethyl, thifensulphuron-methyl, triasulphuron and tribenuron-methyl; thiolcarbamates such as, for example, butylate, cycloate, di-allate, EPTC, esprocarb, molinate, prosulphocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane The active compound according to the invention can furthermore be present in its commercially available formulations and in the use forms prepared from these formulations, as a mixture with synergistic agents. Synergistic agents are compounds which increase the action of the active compounds without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds have an excellent residual action on wood and clay and a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and lschnocerina, for example, Trimenopon spp., Menopon spp., Trinoton spp., Bovicola spp., Werneckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp., From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example Argas spp., Omithodorus spp., Otabius spp., Ixodes spp., Amblyomma spp., Boophilus spp., Derrnacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Octodectes spp., Sarcoptes spp., Notoedres spp., Knemidocoptes spp., Cytodites spp. and Laminosioptes spp.

For example, they show a n outstanding activity against *Boophilus microplus* and *Lucilia cuprina*.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortalit and decreased performance (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for ex ample in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred. but without any limitation:

Beetles, such as

Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec. Tryptodendron spec. Apate monachus, Bostrychus capucins, Heterobostrychus brunneus, Sinoxylon spec., Dinoderus minutus.

Dermapterans, such as

Sirex juvencus, Urocerus gigas, Urocerus gigas taignus, Urocerus augur.

Termites, such as

Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.

Bristletails, such as Lepisma saccharina.

Industrial materials are to be understood as meaning, in the present context, non-live materials such as, preferably, synthetic materials, glues, sizes, paper and board, leather, wood and timber products, and paint.

The materials to be very particularly protected against attack by insects are wood and timber products.

Wood and timber products which can be protected by the composition according to the invention or mixtures comprising such a composition are to be understood as meaning, for example: construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spinde oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Also particularly suitable as a solvent or diluent is water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanide, tolylfluanide, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the examples below.

PREPARATION EXAMPLES

Example Ia-1

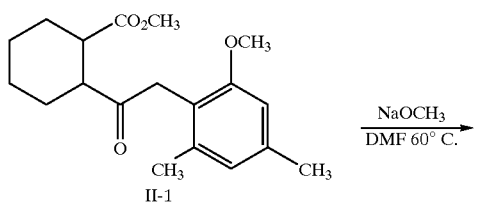

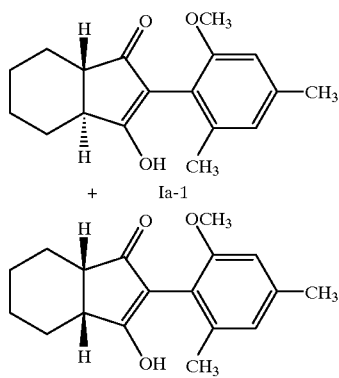

10.5 g of sodium methoxide are added to a solution of the compound of Example II-1 (21 g; 68.6 mmol) in DMF (30 ml), and the mixture is stirred at 60° C. for 2 hours. 5 ml of acetic acid are added and the mixture is concentrated and chromatographed over silica gel (1:1 ethyl acetate:hexane). 5 g (25%) of the compounds shown above are isolated as a cis-trans mixture.

Colourless solid, mp.: 128° C.

Similarly to Example Ia-1 and/or according to the general preparation procedures, the compounds of the formula (Ia) listed in the Table below were prepared:

TABLE 17

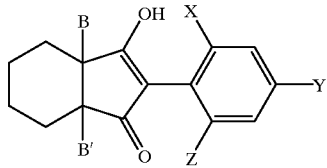

(Ia) B, B' = H

| Ex. | X | Y | Z | mp.: ° C. | Stereochemistry |
|---|---|---|---|---|---|
| I-a-2 | CH₃ | CH₃ | Br | 227 | cis/trans |
| I-a-3 | Cl | Cl | CH₃ | 184 | cis/trans |

TABLE 17-continued (Ia) B, B' = H

| Ex. | X | Y | Z | mp.: ° C. | Stereochemistry |
|---|---|---|---|---|---|
| I-a-4 | C₂H₅ | Br | CH₃ | 168–173 | cis/trans |
| I-a-5 | Cl | CH₃ | CH₃ | 210 | cis/trans |
| I-a-6 | Cl | CH₃ | Cl | 231–233 | cis/trans |
| I-a-7 | CH₃ | Cl | CH₃ | 165–169 | trans |
| I-a-8 | CH₃ | Cl | CH₃ | 147–149 | cis |
| I-a-9 | Cl | H | CH₃ | 131–140 | cis/trans |
| I-a-10 | Cl | H | OCH₃ | 185–189 | cis/trans |
| I-a-11 | Cl | Br | CH₃ | 203–206 | cis/trans |
| I-a-12 | CH₃ | Br | CH₃ | 190–194 | trans |
| I-a-13 | CH₃ | Br | CH₃ | 171–174 | cis |
| I-a-14 | Br | CH₃ | Br | 225–230 | cis/trans |
| I-a-15 | CH₃ | OCH₃ | CH₃ | 162–165 | cis/trans |
| I-a-16 | Br | CH₃ | Cl | 202 | cis/trans |
| I-a-17 | Br | Cl | CH₃ | 228–231 | cis/trans |
| I-a-18 | C₂H₅ | Br | C₂H₅ | 194–197 | trans |
| I-a-19 | C₂H₅ | Br | C₂H₅ | 190–192 | cis |

Example Ib-1

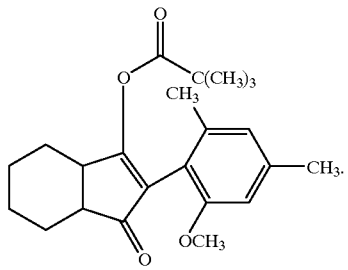

With ice-cooling, a solution of 0.56 ml (4.55 mmol) of pivaloyl chloride in 30 ml of dry methylene chloride is added dropwise to 1.0 g (3.5 mmol) of the compound of Example (Ia-1) and 0.73 ml of triethylamine in 15 ml of dry methylene chloride. The mixture is stirred at room temperature for 2 hours, washed twice with 10% strength aqueous citric acid, and the aqueous acidic phases are extracted with methylene chloride. The combined organic phases are washed twice with 1N NaOH, the aqueous alkaline phases are extracted with methylene chloride and the combined organic phases are finally dried and concentrated.

1.32 g (100% of theory) of the compound shown above are obtained as an oil (isomer mixture).

$^1$H NMR (CDCl₃, 500 MHz); δ=1.12–1.18 (9H); 2.02–2.30 (6H); 3.63–3.73 (3H); 6.48–6.65 (2H).

Similarly, and/or according to the general preparation procedures, the following compounds of the formula (I-b) are obtained:

TABLE 18

![Structure I-b]

(I-b) B, B' = H

| Ex. No. | X | Y | Z | R¹ | Stereo-chemistry | NMR data δ |
|---|---|---|---|---|---|---|
| I-b-2 | Cl | CH₃ | CH₃ | t-C₄H₉— | cis/trans | 1.15(s, 9H, C(CH₃)₃); 6.90(s, 1H, ArH); 7.05(s, 1H, ArH) |
| I-b-3 | C₂H₅ | Br | CH₃ | t-C₄H₉— | cis/trans | 1.10(s, 9H, C(CH₃)₃); 7.2(bs, 2H, ArH) |
| I-b-4 | C₂H₅ | Br | CH₃ | C₂H₅—O—CH₂— | cis/trans | 3.6(bs, 2H, COCH₂O); 7.2(bs, 2H, ArH) |
| I-b-5 | Cl | CH₃ | Cl | t-C₄H₉— | cis/trans | 1.1(bs, 9H, C(CH₃)₃); 7.35(bs, 2H, ArH) |
| I-b-6 | Cl | H | CH₃ | C₂H₅—O—CH₂— | cis/trans | 1.0–1.1(m, 3H, CH₂C$\underline{H}$₃); 2.1–2.2(m, 3H, ArCH₃) |
| I-b-7 | CH₃ | Cl | CH₃ | t-C₄H₉— | trans | 1.1(s, 9H, C(CH₃)₃); 7.0(s, 2H, ArH) |
| I-b-8 | CH₃ | Cl | CH₃ | t-C₄H₉— | cis | 1.1(s, 9H, C(CH₃)₃); 7.0(bs, 2H, ArH) |
| I-b-9 | Cl | H | CH₃ | t-C₄H₉— | cis/trans | 1.1(s, 9H, C(CH₃)₃); 2.1(s, 3H, ArCH₃) |
| I-b-10 | CH₃ | Br | CH₃ | t-C₄H₉— | cis/trans | 1.05(s, 9H, C(CH₃)₃); 7.3(bs, 2H, ArH) |
| I-b-11 | Cl | H | OCH₃ | t-C₄H₉— | cis/trans | 1.15(s, 9H, C(CH₃)₃); 3.7(d, 3H, OCH₃) |
| I-b-12 | CH₃ | OCH₃ | CH₃ | t-C₄H₉— | cis/trans | 1.1(s, 9H, C(CH₃)₃); 6.6(d, 2H, ArH) |
| I-b-13 | Br | CH₃ | Cl | t-C₄H₉— | cis/trans | 1.15(bs, 9H, C(CH₃)₃); 2.3(m, 3H, ArCH₃) |
| I-b-14 | C₂H₅ | Br | C₂H₅ | t-C₄H₉— | cis/trans | 1.1(s, 9H, C(CH₃)₃); 7.2(m, 2H, ArH) |
| I-b-15 | C₂H₅ | Br | C₂H₅ | C₂H₅—O—CH₂— | trans | 4.1(s, 2H, COCH₂O); 7.2(bs, 2H, ArH) |

Example Ic-1

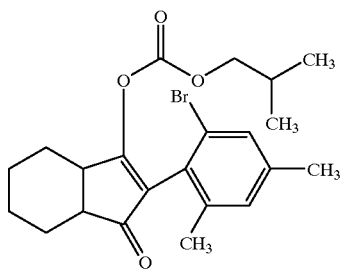

With ice-cooling, a solution of 0.59 ml (4.55 mmol) of isobutyl chloroformate in 3 ml of dry methylene chloride are added dropwise to 1.17 g (3.5 mmol) of the compound of Example (Ia-2) and 0.73 ml of triethylamine in 15 ml of dry methylene chloride. The mixture is stirred at room temperature for 2 hours and then worked-up as in Example (Ib-1).

1.55 g (100% of theory) of the compound shown above are obtained as an oil (isomer mixture).

$^1$H NMR (CDCl₃, 500 MHz) δ=0.85–0.90 (6H); 2.10–2.30 (6H); 3.85–3.95 (2H); 6.97–7.24 (2 H).

Similarly, and/or according to the general preparation procedures, the following compounds of the formula (I-c) are obtained:

TABLE 19

(I-c) B, B' = H

| Ex. No. | X | Y | Z | M | $R^2$ | Stereo-chemistry | NMR data δ (ppm) |
|---|---|---|---|---|---|---|---|
| I-c-2 | Cl | $CH_3$ | $CH_3$ | O | i-$C_4H_9$— | cis/trans | 0.8–1.0(m, 3H, $CH_2CH_3$); 7.0(d, 2H, ArH) |
| I-c-3 | Cl | $CH_3$ | $CH_3$ | S | i-$C_3H_7$— | cis/trans | 1.2–1.3(m, 6H, $CH(CH_3)_2$); 7.0(d, 2H, ArH) |
| I-c-4 | $C_2H_5$ | Br | $CH_3$ | O | i-$C_4H_9$— | cis/trans | 4.5–4.7(m, 1H, OCH); 7.2(bs, 2H, ArH) |
| I-c-5 | $C_2H_5$ | Br | $CH_3$ | S | i-$C_3H_7$— | cis/trans | 1.2–1.4(m, 6H, $CH(CH_3)_2$); 7.2(d, 2H, ArH) |
| I-c-6 | Cl | $CH_3$ | Cl | O | i-$C_4H_9$— | cis/trans | 4.6–4.7(m, 1H, OCH); 7.35(s, 2H, ArH) |
| I-c-7 | $CH_3$ | Cl | $CH_3$ | O | i-$C_4H_9$— | cis | 4.5–4.6(m, 1H, OCH); 7.05(bs, 2H, ArH) |
| I-c-8 | $CH_3$ | Cl | $CH_3$ | S | i-$C_3H_7$— | cis | 1.2–1.3(m, 6H, $CH(CH_3)_2$; 7.05(s, 2H, ArH) |
| I-c-9 | Cl | H | $CH_3$ | O | i-$C_4H_9$— | cis/trans | 2.1(m, 3H, Ar$CH_3$); 4.5–4.7(m, 1H, OCH) |
| I-c-10 | Cl | H | $CH_3$ | S | i-$C_3H_7$— | cis/trans | 1.2–1.3(m, 6H, $CH(CH_3)_2$; 2.1(m, 3H, Ar$CH_3$) |
| I-c-11 | Cl | H | $OCH_3$ | O | i-$C_4H_9$— | cis/trans | 3.75(d, 3H, $OCH_3$); 4.6–4.7(m, 1H, OCH) |
| I-c-12 | $CH_3$ | $OCH_3$ | $CH_3$ | O | i-$C_4H_9$— | cis/trans | 4.5–4.6(m, 1H, OCH); 6.6(s, 2H, ArH) |
| I-c-13 | $CH_3$ | Br | $CH_3$ | O | i-$C_4H_9$— | cis/trans | 4.5–4.6(m, 1H, OCH); 7.3(s, 2H, ArH) |
| I-c-14 | $CH_3$ | Br | $CH_3$ | S | i-$C_3H_7$— | cis/trans | 1.1–1.2(m, 6H, $CH(CH_3)_2$); 7.3(s, 2H, ArH) |
| I-c-15 | $C_2H_5$ | Br | $C_2H_5$ | O | s-$C_4H_9$— | cis | 4.6–4.7(m, 1H, OCH); 7.3(s, 2H, ArH) |
| I-c-16 | $C_2H_5$ | Br | $C_2H_5$ | S | i-$C_3H_7$— | cis | 0.95–1.05(m, 6H, $CH(CH_3)_2$; 7.3(s, 2H, ArH) |

Example Id-1

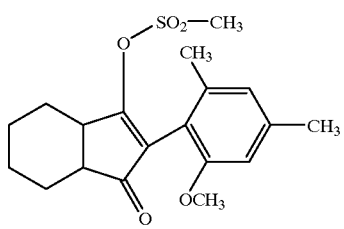

With ice-cooling, a solution of 0.35 ml (4.55 mmol) of methanesulphonyl chloride in 3 ml of dry methylene chloride are added dropwise to 1.0 g (3.5 mmol) of the compound of Example (Ia-1) and 0.73 ml of triethylamine in 15 ml of dry methylene chloride. The mixture is stirred at room temperature for 2 hours and then worked-up as in Example (Ib-1). The residue which remains after concentrating the organic phases is stirred with cyclohexane/ethyl acetate 3/1, and the colorant is filtered off with suction and dried.

Yield: 0.50 g (39% of theory); mp.: 132° C.

PREPARATION OF THE STARTING MATERIALS

Example II-1

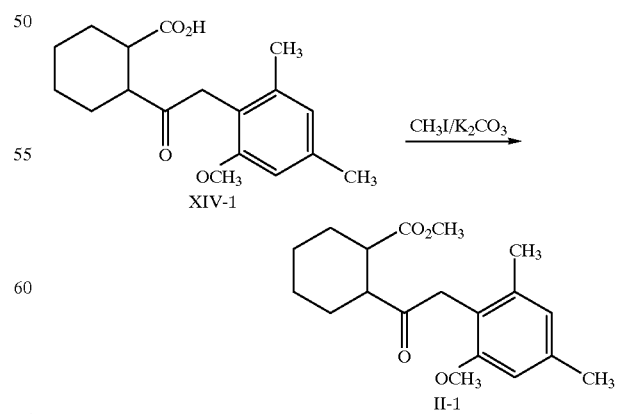

A mixture of the compound of Example XIV-1 (33 g, 113 mmol), potassium carbonate (46 g), acetone (460 ml) and iodomethane (46 ml) is heated under reflux for 5 hours, diluted with ethyl ether (100 ml), filtered through silica gel and concentrated. The residue is chromatographed (silica gel, $CH_2C_2$: petroleum ether 1:1). 21 g (60%) of a colourless oil are obtained.

$^1$H-NMR ($CDCl_3$, δ ppm): 6.62 (bs, 1H); 6.53 (bs, 1H); 3.74 (s, 3H); 3.60 (s, 3H).

Similarly to Example II-1 and/or according to the general preparation procedures, the compounds of the formula (II) listed in Table 20 were prepared:

TABLE 20

(II) B, B' = H

| Ex. | X | Y | Z | $^1$HNMR($CDCl_3$, δ ppm) |
|---|---|---|---|---|
| II-2 | $CH_3$ | $CH_3$ | Br | 7.22(s, 1H); 6.91(s, 1H); 3.61(s, 3H); 2.26(s, 3H) |
| II-3 | Cl | Cl | $CH_3$ | 7.23(s, 1H); 7.08(s, 1H); 3.62(s, 3H); 2.21(s, 3H) |
| II-4 | $C_2H_5$ | Br | $CH_3$ | 2.15(s, 3H, $ArCH_3$); 7.18(d, 2H, ArH) |
| II-5 | Cl | $CH_3$ | $CH_3$ | 2.10/2.22(s, 6H, $ArCH_3$); 6.95/7.08(s, 2H, ArH) |
| II-6 | Cl | $CH_3$ | Cl | 2.29(s, 3H, $ArCH_3$); 7.28(s, 2H, ArH) |
| II-7 | $CH_3$ | Cl | $CH_3$ | 2.16(s, 6H, $ArCH_3$); 7.00(s, 2H, ArH) |
| II-8 | Cl | H | $CH_3$ | 2.14(s, 3H, $ArCH_3$); 7.1–7.3(m, 3H, ArH) |
| II-9 | Cl | H | $OCH_3$ | 3.77(s, 3H, $ArOCH_3$); 6.7–7.2(m, 3H, ArH) |
| II-10 | Cl | Br | $CH_3$ | 2.21(s, 3H, $ArCH_3$); 7.23/7.38(s, 2H, ArH) |
| II-11 | $CH_3$ | Br | $CH_3$ | 2.09(s, 3H, $ArCH_3$); 7.20(s, 2H, ArH) |
| II-12 | Br | $CH_3$ | Br | 2.26(s, 3H, $ArCH_3$); 7.32(s, 2H, ArH) |
| II-13 | $CH_3$ | $OCH_3$ | $CH_3$ | 2.07(s, 6H, $ArCH_3$); 6.58(s, 2H, ArH) |
| II-14 | Br | $CH_3$ | Cl | 2.29(s, 3H, $ArCH_3$); 7.32/7.45(s, 2H, ArH) |
| II-15 | Br | Cl | $CH_3$ | 2.22(s, 3H, $ArCH_3$); 7.12/7.41(s, 2H, ArH) |
| II-16 | $C_2H_5$ | Br | $C_2H_5$ | 2.47(q, 4H, $ArCH_2$); 7.19(s, 2H, ArH) |

Example XIV-1

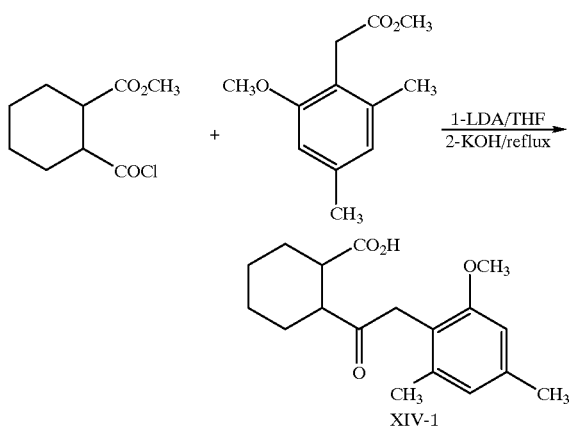

XIV-1

24.8 g (119 mmol) of methyl 2,4-dimethyl-6-methoxyphenylacetate are added to a solution of lithium diisopropylamide (130 mmol) in tetrahydrofuran (THF) (100 ml). After 30 minutes at room temperature, 17 g of methyl 3,4-tetramethylene succinate chloride are added and the mixture is stirred at room temperature (1 hour). 100 ml of water and 30 g of ammonium chloride are then added. The intermediate is extracted with ether and filtered through silica gel. After concentration, the residue (oil, 44 g) is boiled under reflux with 88 g of potassium hydroxide and 250 ml of water (2 days). The mixture is cooled and acidified (conc. HCl) and the solid is filtered off, giving 33 g of the compound XIV-1 shown above. Colourless solid, mp.: 128° C.

Similarly to Example XIV-1 and/or according to the general preparation procedures, the compounds of the formula (XIV) listed in Table 21 were prepared:

TABLE 21

| Ex | X | Y | Z | $^1$HNMR ($CDCl_3$, δ ppm) |
|---|---|---|---|---|
| XIV-3 | Cl | Cl | $CH_3$ | 3.85 (s, 2H); 2.80 (m, 2H) |
| XIV-2 | $CH_3$ | $CH_3$ | Br | 6.93 (s, 1H); 7.25 (s, 1H); 2.80 (m, 2H) |

In some instances, the compounds of the formula (XIV)

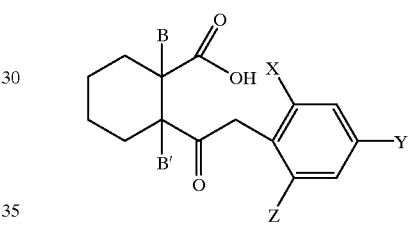

(XIV)

in which

B, B', X, Y and Z are each as defined above were employed as crude products in the synthesis of the compounds of the formula (II).

USE EXAMPLES

Example A

Tetranychus Test (resistent)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are heavily infested by all development stages of the greenhouse red spider mite (Tetranychus urticae) are treated by being dipped into a preparation of the active compound of the desired concentration.

After the desired period of time, the kill in % is determined. 100% means that all the spider mites have been killed; 0% means that none of the spider mites have been killed.

In this test, for example the compound of Preparation Example Ia-1, at an exemplary active compound concentration of 0.01%, effected a kill of 100% after 13 days.

Example B

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration. Cabbage leaves (Brassica oleracea) are treated by being dipped into a preparation of the active compound of the desired concentration and populated with mustard beetle larvae (Phaedon cochleariae) while the leaves are still moist.

After the desired period of time, the kill in % is determined. 100% means that all beetle larvae have been killed; 0% means that none of the beetle larvae have been killed.

In this test, for example the compounds of Preparation Examples Ia-1, Ia-2 and Ia-3, at an exemplary active compound concentration of 0.1%, effected a kill of 100% after 7 days.

Example C

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into a preparation of the active compound of the desired concentration and populated with caterpillars of the diamond-back moth (Plutella maculipennis) while the leaves are still moist.

After the desired period of time, the kill in % is determined. 100% means that all caterpillars have been killed; 0% means that none of the caterpillars have been killed.

In this test, for example the compounds of Preparation Examples Ia-1, Ia-2 and Ia-3, at an exemplary active compound concentration of 0.1%, effected a kill of 100% after 7 days.

Example D

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (Oryza sativa) are treated by being dipped into a preparation of the active compound of the desired concentration and populated with green rice leaf hoppers (Nephotettix cincticeps) while the seedlings are still moist.

After the desired period of time, the kill in % is determined. 100% means that all leaf hoppers have been killed; 0% means that none of the leaf hoppers have been killed.

In this test, for example the compounds of Preparation Examples Ia-1, Ia-2 and Ia-3, at an exemplary active compound concentration of 0.1%, effected a kill of 100% after 6 days.

Example E

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is advantageous to keep the amount of water per unit area constant. The concentration of the active compound in the preparation is immaterial, only the amount of active compound applied per unit area matters. After three weeks, the degree of damage to the plants is scored visually in % damage by comparison with the development of the untreated control. The figures denote:

0%=no effect (like untreated control)
100%=total destruction

In this test, at an exemplary application rate of 60 g/ha, for example the compound of Preparation Example Ia-1 showed at least 90% activity against Alopecurus, Bromus, Sorghum and Matricaria and was tolerated very well by barley and cotton.

In this test, at an exemplary application rate of 250 g/ha, for example the compound of Preparation Example Ia-2 showed 100% activity against Alopecurus, Setaria and Sinapis.

In this test, at an exemplary application rate of 250 g/ha, for example the compound of Preparation Example Ia-3 showed an activity of 80% against Alopecurus and was tolerated very well by sugar beet.

Example F

Myzus Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) which are heavily infested by peach aphids (Myzus persicae) are treated by being dipped into a preparation of the active compound of the desired concentration.

After the desired period of time, the kill in % is determined. 100% means that all aphids have been killed; 0% means that none of the aphids have been killed.

In this test, for example the compounds of Preparation Examples Ia-1, Ia-2 and Ia-3, at an exemplary active compound concentration of 0.1%, effected a kill of at least 90% after 6 days.

What is claimed is:

1. A compound of the formula (I)

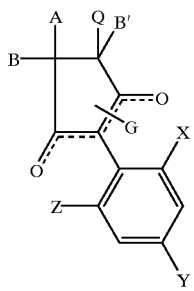

in which

- X represents halogen, $C_1$–$C_6$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_1$–$C_6$-halogenoalkoxy, $C_2$–$C_6$-halogenoalkenyloxy, nitro, cyano or respectively optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, benzyloxy or benzylthio,
- Y represents hydrogen, halogen, $C_1$–$C_6$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkoxy, $C_2$–$C_6$-halogenoalkenyloxy, nitro or cyano,
- Z represents halogen, $C_1$–$C_6$-alkyl, $C_2$–$C_6$-alkenyl, $C_1$–$C_6$-alkoxy, $C_2$–$C_6$-alkenyloxy, $C_1$–$C_6$-halogenoalkyl, $C_1$–$C_6$-halogenoalkoxy, $C_2$–$C_6$-halogenoalkenyloxy, nitro or cyano,
  where X, Y and Z do not simultaneously represent methyl,
- A and Q together represent $C_1$–$C_6$-alkanediyl or $C_2$–$C_6$-alkenediyl, each of which is unsubstituted or mono- to trisubstituted by identical or different substituents from the group consisting of halogen, hydroxyl, mercapto, and of $C_1$–$C_{10}$-alkyl, $C_1$–$C_6$-alkoxy, $C_1$–$C_6$-alkylthio, $C_3$–$C_7$-cycloalkyl, each of which is unsubstituted or mono- to nonasubstituted by identical or different halogens, and of benzyloxy and phenyl, each of which is unsubstituted or mono- to pentasubstituted by identical or different substituents from the group consisting of halogen, $C_1$–$C_6$-alkyl and $C_1$–$C_6$-alkoxy, the $C_1$–$C_6$-alkanediyl or the $C_2$–$C_6$-alkenediyl containing or not containing one of the groups below

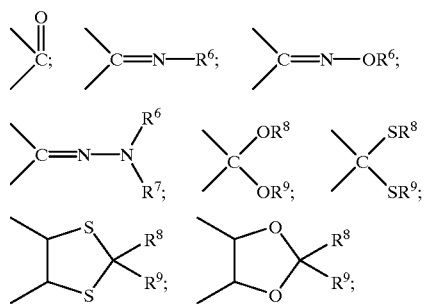

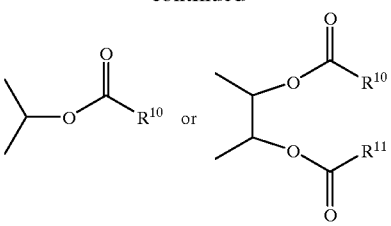

or bridged or not bridged by a $C_1$–$C_2$-alkanediyl group,
- B and B' independently of one another each represent hydrogen, halogen or $C_1$–$C_6$-alkyl or together represent respectively unsubstituted or $C_1$–$C_6$-alkyl-substituted $C_1$–$C_6$-alkanediyl or $C_2$–$C_4$-alkenediyl,
- G represents hydrogen (a) or represents one of the groups

(b)

(c)

(d)

(e)

E or
(f)

(g)

in which
- E represents a metal ion equivalent or an ammonium ion,
- L represents oxygen or sulphur and
- M represents oxygen or sulphur,
- $R^1$ represents $C_1$–$C_{20}$-alkyl, $C_2$–$C_{10}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl, each of which is unsubstituted or mono- or polysubstituted by identical or different halogens, or represents $C_3$–$C_8$-cycloalkyl which is unsubstituted or mono- or polysubstituted by identical or different substituents from the group consisting of halogen, $C_1$–$C_6$-alkyl and $C_1$–$C_6$-alkoxy and in which at least one methylene group is or is not replaced by an atom independently selected from the group consisting of oxygen and sulphur,
  represents phenyl which is unsubstituted or mono- or polysubstituted by identical or different substituents from the group consisting of halogen, nitro, cyano, $C_1$–$C_6$-alkyl, $C_1$–$C_6$-alkoxy, $C_1$–$C_6$-halogenoalkyl and $C_1$–$C_6$-halogenoalkoxy,
  represents phenyl-$C_1$–$C_6$-alkyl which is unsubstituted or mono- or polysubstituted by identical or different substituents from the group consisting of halogen, $C_1$–$C_6$-alkyl, $C_1$–$C_6$-alkoxy, $C_1$–$C_6$-halogenoalkyl and $C_1$–$C_6$-halogenoalkoxy, represents hetaryl which is unsubstituted or mono- or polysubstituted by identical or different substituents from the group consisting of halogen and $C_1$–$C_6$-alkyl and has 5 or 6 ring atoms and one to three hetero atoms from the group consisting of oxygen, sulphur and nitrogen, represents phenoxy-$C_1$–$C_6$-alkyl which is unsubstituted or mono- or polysubstituted by identical or different substituents from the group consisting of halogen and $C_1$–$C_6$-alkyl, or represents hetaryloxy-$C_1$–$C_6$-alkyl which is unsubstituted or mono- or polysubstituted by identical or different substituents from the group consisting of halogen, amino and $C_1$–$C_6$-alkyl and has 5 or 6 ring atoms and one to three hetero atoms from the group consisting of oxygen, sulphur and nitrogen, $R^2$ represents $C_1$–$C_{20}$-alkyl, $C_2$–$C_{10}$-alkenyl, $C_1$–$C_8$-alkoxy-$C_2$–$C_8$-alkyl or poly-$C_1$–$C_8$-alkoxy-$C_2$–$C_8$-alkyl, each of which is unsubstituted or mono- or polysubstituted by identical or different halogens, represents $C_3$–$C_6$-cycloalkyl which is unsubstituted or mono- or poly-substituted by identical or different substituents from the group consisting of halogen, $C_1$–$C_6$-alkyl and $C_1$–$C_6$-alkoxy, or represents phenyl or benzyl, each of which is unsubstituted or mono- or polysubstituted by identical or different substituents from the group consisting of halogen, nitro, cyano, $C_1$–$C_6$-alkyl, $C_1$–$C_6$-alkoxy, $C_1$–$C_3$-halogenoalkoxy and $C_1$–$C_3$-halogenoalkyl, $R^3$ represents $C_1$–$C_{12}$-alkyl, each of which is unsubstituted or mono- or polysubstituted by identical or different halogens, or represents phenyl or phenyl-$C_1$–$C_4$-alkyl, each of which is unsubstituted or mono- or polysubstituted by identical or different substituents from the group consisting of halogen, $C_1$–$C_6$-alkyl, $C_1$–$C_6$-alkoxy, $C_1$–$C_3$-halogenoalkyl, $C_1$–$C_3$-halogenoalkoxy, cyano and nitro, $R^4$ and $R^5$ independently of one another each represent $C_1$–$C_8$-alkyl, $C_1$–$C_8$-alkoxy, $C_1$–$C_8$-alkylamino, di-($C_1$–$C_8$-alkyl)-amino, $C_1$–$C_8$-alkylthio, $C_3$–$C_5$-alkenylthio, $C_3$–$C_7$-cycloalkylthio, each of which is unsubstituted or mono- or polysubstituted by identical or different halogens, or represents phenyl, phenoxy or phenylthio, each of which is unsubstituted or mono- or polysubstituted by identical or different substituents from the group consisting of halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl and $C_1$–$C_4$-halogenoalkyl, $R^6$ represents hydrogen, represents $C_1$–$C_{10}$-alkyl, $C_3$–$C_8$-alkenyl, $C_1$–$C_8$-alkoxy-$C_2$–$C_8$-alkyl, each of which is unsubstituted or mono- or polysubstituted by identical or different halogens, represents $C_3$–$C_{10}$-cycloalkyl which is unsubstituted or mono- or polysubstituted by identical or different substituents from the group consisting of halogen, $C_1$–$C_6$-alkyl, $C_1$–$C_6$-alkoxy, $C_1$–$C_3$-halogenoalkyl and $C_1$–$C_3$-halogenoalkoxy, represents phenyl which is unsubstituted or mono- or polysubstituted by identical or different substituents from the group consisting of halogen, $C_1$–$C_3$-halogenoalkyl, $C_1$–$C_8$-alkyl, $C_1$–$C_3$-halogenoalkoxy and $C_1$–$C_8$-alkoxy, or represents benzyl which is unsubstituted or mono- or polysubstituted by identical or different substituents from the group consisting of halogen, $C_1$–$C_8$-alkyl, $C_1$–$C_3$-halogenoalkyl, $C_1$–$C_3$-halogenoalkoxy and $C_1$–$C_8$-alkoxy, $R^7$ represents hydrogen or represents $C_1$–$C_{10}$-alkyl or $C_3$–$C_{10}$-alkenyl, each of which is unsubstituted or mono- or polysubstituted by identical or different halogens, or $R^6$ and $R^7$ combine with the linking N-atom to form an unsubstituted or oxygen- or sulphur-containing and optionally $C_1$–$C_6$-alkyl-substituted 3- to 7-membered ring, $R^8$ and $R^9$ independently of one another each represent hydrogen, represent $C_1$–$C_6$-alkyl which is unsubstituted or mono- or polysubstituted by identical or different halogens or represent phenyl or phenyl-$C_1$–$C_4$-alkyl, each of which is unsubstituted or mono- or polysubstituted by identical or different substituents from the group consisting of halogen, $C_1$–$C_6$-alkyl, $C_1$–$C_6$-alkoxy, $C_1$–$C_6$-halogenoalkyl, $C_1$–$C_6$-halogenoalkoxy, nitro and cyano, or together represent $C_2$–$C_6$-alkanediyl which is unsubstituted or mono- or polysubstituted by identical or different substituents from the group consisting of halogen, $C_1$–$C_6$-alkyl, $C_1$–$C_6$-alkoxy and $C_1$–$C_3$-halogenoalkyl, and $R^{10}$ and $R^{11}$ independently of one another each represent $C_1$–$C_{10}$-alkyl, $C_2$–$C_{10}$-alkenyl, $C_1$–$C_{10}$-alkoxy, $C_1$–$C_{10}$-alkylamino, di-($C_1$–$C_{10}$-alkyl)-amino, $C_3$–$C_{10}$-alkenylamino, di-($C_3$–$C_{10}$-alkenyl)-amino, each of which is unsubstituted or mono- or polysubstituted by identical or different halogens, or represent phenyl or benzyl, each of which is mono- or polysubstituted by identical or different substituents from the group consisting of halogen, $C_1$–$C_4$-alkyl, $C_1$–$C_4$-alkoxy, $C_1$–$C_4$-halogenoalkyl, nitro and cyano.

2. A compound of the formula (I) according to claim 1, in which

X represents fluorine, chlorine, bromine, $C_1$–$C_4$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulphinyl, $C_1$–$C_4$-alkylsulphonyl, $C_1$–$C_4$-halogenoalkyl, $C_1$–$C_4$-halogenoalkoxy, $C_2$–$C_4$-halogenoalkenyloxy, nitro, cyano or respectively fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted or unsubstituted phenyl, phenoxy, phenylthio, benzyloxy or benzylthio, Y represents hydrogen, fluorine, chlorine, bromine, $C_1$–$C_4$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulphinyl, $C_1$–$C_4$-alkylsulphonyl, $C_1$–$C_4$-halogenoalkyl, $C_1$–$C_4$-halogenoalkoxy, $C_2$–$C_4$-halogenoalkenyloxy, nitro or cyano, Z represents fluorine, chlorine, bromine, $C_1$–$C_4$-alkyl, $C_2$–$C_4$-alkenyl, $C_1$–$C_4$-alkoxy, $C_2$–$C_4$-alkenyloxy, $C_1$–$C_4$-halogenoalkyl, $C_1$–$C_4$-halogenoalkoxy, $C_2$–$C_4$-halogenoalkenyloxy, nitro or cyano, where X, Y and Z do not simultaneously represent methyl, A and Q together represent $C_1$–$C_5$-alkanediyl or $C_2$–$C_5$-alkenediyl, each of which is unsubstituted or mono- or disubstituted by identical or different substituents from the group consisting of fluorine, chlorine, bromine, hydroxyl, mercapto, and of $C_1$–$C_8$-alkyl, $C_1$–$C_4$-alkoxy, $C_1$–$C_4$-alkylthio, $C_5$–$C_7$-cycloalkyl or phenyl, each of which is unsubstituted or mono- to pentasubstituted by identical or different substituents from the group consisting of fluorine and chlorine, the $C_1$–$C_5$-alkanediyl or the $C_2$–$C_5$-alkenediyl containing or not containing one of the groupings below

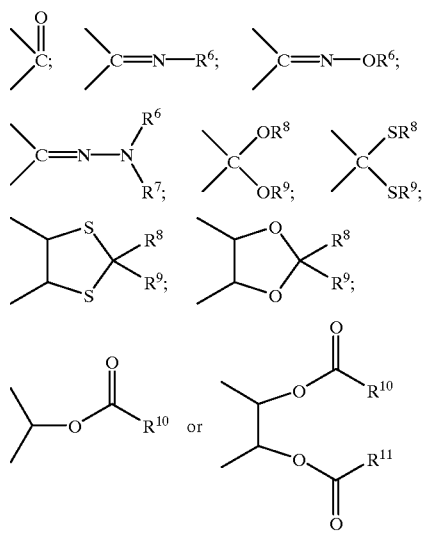

or bridged or not bridged by a $C_1$–$C_2$-alkanediyl group,

B and B' independently of one another each represent hydrogen, fluorine, chlorine or $C_1$–$C_4$-alkyl or together represent respectively unsubstituted or $C_1$–$C_4$-alkyl-substituted $C_1$–$C_5$-alkanediyl or $C_2$–$C_4$-alkenediyl, G represents hydrogen (a) or one of the groups

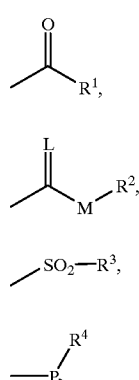

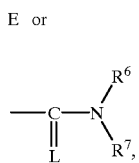

in which

E represents a metal ion equivalent or an ammonium ion,

L represents oxygen or sulphur and

M represents oxygen or sulphur, $R^1$ represents $C_1$–$C_{16}$-alkyl, $C_2$–$C_8$-alkenyl, $C_1$–$C_6$-alkoxy-$C_1$–$C_6$-alkyl, $C_1$–$C_6$-alkylthio-$C_1$–$C_6$-alkyl, poly-$C_1$–$C_6$-alkoxy-$C_1$–$C_6$-alkyl, each of which is unsubstituted or mono- to nonasubstituted by identical or different substituents from the group consisting of fluorine and chlorine, or represents $C_3$–$C_7$-cycloalkyl which is unsubstituted or mono- to trisubstituted by identical or different substituents from the group consisting of fluorine, chlorine, $C_1$–$C_4$-alkyl and $C_1$–$C_4$-alkoxy and in which one or two not directly adjacent methylene groups is or is not replaced by an atom independently selected from the group consisting of oxygen and sulphur, represents phenyl which is unsubstituted or mono- to trisubstituted by identical or different substituents from the group consisting of fluorine, chlorine, bromine, cyano, nitro, $C_1$–$C_4$-alkyl, $C_1$–$C_4$-alkoxy, $C_1$–$C_3$-halogenoalkyl and $C_1$–$C_3$-halogenoalkoxy, represents phenyl-$C_1$–$C_4$-alkyl which is unsubstituted or mono- to trisubstituted by identical or different substituents from the group consisting of fluorine, chlorine, bromine, $C_1$–$C_4$-alkyl, $C_1$–$C_4$-alkoxy, $C_1$–$C_3$-halogenoalkyl and $C_1$–$C_3$-halogenoalkoxy, represents ftiranyl, thienyl, pyridyl, pyrimidyl, thiazolyl or pyrazolyl, each of which is unsubstituted or mono- or disubstituted by identical or different substituents from the group consisting of fluorine, chlorine, bromine and $C_1$–$C_4$-alkyl, represents phenoxy-$C_1$–$C_5$-alkyl which is unsubstituted or mono- to trisubstituted by identical or different substituents from the group consisting of fluorine, chlorine and $C_1$–$C_4$-alkyl, or represents pyridyloxy-$C_1$–$C_6$-alkyl, pyrimidinyloxy-$C_1$–$C_6$-alkyl or thiazolyloxy-$C_1$–$C_6$-alkyl, each of which is unsubstituted or mono- or di substituted by identical or different substituents from the group consisting of fluorine, chlorine, amino and $C_1$–$C_4$-alkyl, $R^2$ represents $C_1$–$C_6$-alkyl, $C_2$–$C_8$-alkenyl, $C_1$–$C_6$-alkoxy-$C_2$–$C_6$-alkyl or poly-$C_1$–$C_6$-alkoxy-$C_2$–$C_6$-alkyl, each of which is unsubstituted or mono- to heptasubstituted by identical or different substituents from the group consisting of fluorine and chlorine, represents $C_3$–$C_6$-cycloalkyl which is unsubstituted or mono- to trisubstituted by identical or different substituents from the group consisting of fluorine, chlorine, $C_1$–$C_4$-alkyl and $C_1$–$C_4$-alkoxy, or represents phenyl or benzyl, each of which is unsubstituted or mono- to trisubstituted by identical or different substituents from the group consisting of fluorine, chlorine, bromine, nitro, cyano, $C_1$–$C_4$-alkyl, $C_1$–$C_4$-alkoxy, $C_1$–$C_2$-halogenoalkoxy and $C_1$–$C_2$-halogenoalkyl, $R^3$ represents $C_1$–$C_9$-alkyl, which is unsubstituted or mono- to pentasubstituted by identical or different substituents from the group consisting of fluorine and chlorine, or represents phenyl or phenyl-$C_1$–$C_2$-alkyl, each of which is unsubstituted or mono- to trisubstituted by identical or different substituents from the group consisting of fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano and nitro, $R^4$ and $R^5$ independently of one another represent $C_1$–$C_6$-alkyl, $C_1$–$C_6$-alkoxy, $C_1$–$C_6$-alkylamino, di-($C_1$–$C_6$-alkyl)-amino, $C_1$–$C_6$-alkylthio, $C_3$–$C_4$-alkenylthio, $C_3$–$C_6$-cycloalkylthio, each of which is unsubstituted or mono- to pentasubstituted by identical or different substituents from the group consisting of fluorine and chlorine, or represents phenyl, phenoxy or phenylthio, each of which is unsubstituted or mono- to trisubstituted by identical or different substituents from the group consisting of fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl and $C_1$–$C_3$-halogenoalkyl, $R^6$ represents hydrogen, represents $C_1$–$C_8$-alkyl, $C_3$–$C_6$-alkenyl, $C_1$–$C_6$-alkoxy-$C_2$–$C_6$-alkyl, each of which is unsubstituted or mono- to pentasubstituted by identical or different substituents from the group consisting of fluorine and chlorine, represents $C_3$–$C_8$-cycloalkyl which is unsubstituted or mono- to trisubstituted by identical or different substituents from the group consisting of fluorine, chlorine, $C_1$–$C_4$-alkyl, $C_1$–$C_4$-alkoxy, $C_1$–$C_2$-halogenoalkyl and $C_1$–$C_2$-halogenalkoxy, represents phenyl which is unsubstituted or mono- to trisubstituted by identical or different substituents from the group consisting of fluorine, chlorine, bromine, $C_1$–$C_2$-halogenoalkyl, $C_1$–$C_5$-alkyl, $C_1$–$C_2$-halogenoalkoxy and $C_1$–$C_5$-alkoxy, or represents benzyl which is unsubstituted or mono- to trisubstituted by identical or different substituents from the group consisting of fluorine, chlorine, bromine, $C_1$–$C_5$-alkyl, $C_1$–$C_2$-halogenoalkyl, $C_1$–$C_2$-halogenoalkoxy and $C_1$–$C_5$-alkoxy, $R^7$ represents hydrogen or represents $C_1$–$C_8$-alkyl or $C_3$–$C_8$-alkenyl, each of which is unsubstituted or mono- to pentasubstituted by identical or different substituents from the group consisting of fluorine and chlorine, or $R^6$ and $R^7$ combine with the linking N-atom to form a 4- to 7-membered ring containing or not containing oxygen- or sulphur and unsubstituted or substituted by $C_1$–$C_4$-alkyl, $R^8$ and $R^9$ independently of one another each represent hydrogen, $C_1$–$C_4$-alkyl which is unsubstituted or mono- to pentasubstituted by identical or different substituents from the group consisting of fluorine and chlorine, or represent phenyl which is unsubstituted or mono- to trisubstituted by identical or different substituents from the group consisting of fluorine, chlorine, $C_1$–$C_4$-alkyl, $C_1$–$C_4$-alkoxy, $C_1$–$C_2$-halogenoalkyl, $C_1$–$C_2$-halogenoalkoxy, nitro and cyano, or together represent $C_2$–$C_5$-alkanediyl which is unsubstituted or mono- to trisubstituted by identical or different substituents from the group consisting of fluorine, chlorine, $C_1$–$C_4$-alkyl, $C_1$–$C_4$-alkoxy and $C_1$–$C_2$-halogenoalkyl, and $R^{10}$ and $R^{11}$ independently of one another each represent $C_1$–$C_8$-alkyl, $C_2$–$C_8$-alkenyl, $C_1$–$C_8$-alkoxy, $C_1$–$C_8$-alkylamino, $C_3$–$C_8$-alkenylamino, di-($C_1$–$C_8$-alkyl)-amino or di-($C_3$–$C_8$-alkenyl)-amino, each of which is unsubstituted or mono- to pentasubstituted by identical or different substituents from the group consisting of fluorine and chlorine.

3. A compound of the formula (I) according to claim 1, in which

X represents fluorine, chlorine, bromine, methyl, ethyl, propyl, isopropyl, ethenyl, 1-propenyl, methoxy, ethoxy, propoxy, isopropoxy, allyloxy, methallyloxy, trifluoromethyl, difluoromethoxy, trifluoromethoxy, trifluoroethoxy, methylthio, methylsulphinyl, methylsulphonyl, nitro, cyano, or respectively optionally fluorine-, chlorine-, bromine-, methyl-, ethyl-, propyl-, isopropyl-, tert-butyl-, methoxy-, ethoxy-, propoxy-, tert-butoxy-, trifluoromethyl-, trifluoromethoxy-, nitro- or cyano-substituted phenyl, phenoxy, phenylthio, benzyloxy or benzylthio, Y represents hydrogen, fluorine, chlorine, bromine, methyl, ethyl, n-propyl, i-propyl, n-butyl, i-butyl, tert-butyl, ethenyl, 1-propenyl, methoxy, ethoxy, propoxy, isopropoxy, allyloxy, methallyloxy, trifluoromethyl, methylthio, methylsulphinyl, methylsulphonyl, difluoromethoxy, trifluoromethoxy, trifluoroethoxy, nitro or cyano, Z represents fluorine, chlorine, bromine, methyl, ethyl, n-propyl, i-propyl, n-butyl, i-butyl, tert-butyl, ethenyl, 1-propenyl, methoxy, ethoxy, propoxy, isopropoxy, allyloxy, methallyloxy, trifluoromethyl, difluoromethoxy, trifluoromethoxy, trifluoroethoxy, nitro or cyano, where X, Y and Z do not simultaneously represent methyl, A and Q together represent $C_1$–$C_4$-alkanediyl or $C_2$–$C_4$-alkenediyl, each of which is optionally mono- or disubstituted by identical or different substituents from the group consisting of fluorine, chlorine, hydroxyl, and of $C_1$–$C_6$-alkyl and $C_1$–$C_6$-alkoxy, each of which is unsubstituted or mono- to trisubstituted by identical or different substituents from the group consisting of fluorine and chlorine, B and B' independently of one another each represent hydrogen, methyl or ethyl, G represents hydrogen (a) or represents one of the groups (b)
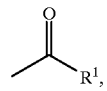

(c)
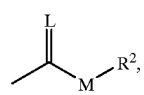

(d)
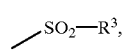

(e)
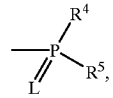

(f)
E or (g)
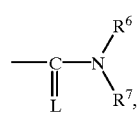

in which

E represents a metal ion equivalent or an ammonium ion,

L represents oxygen or sulphur and

M represents oxygen or sulphur, $R^1$ represents $C_1$–$C_{14}$-alkyl, $C_2$–$C_6$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl, each of which is unsubstituted or mono- to pentasubstituted by identical or different substituents from the group consisting of fluorine and chlorine, or represents $C_3$–$C_6$-cycloalkyl which is optionally mono- or disubstituted by identical or different substituents from the group consisting of fluorine, chlorine, methyl, ethyl, methoxy and ethoxy and in which one or two not directly adjacent methylene groups are or are not replaced by oxygen, or an oxygen atom and a sulfur atom, represents phenyl which is unsubstituted or mono- or disubstituted by identical or different substituents from the group consisting of fluorine, chlorine, bromine, methyl, ethyl, propyl, i-propyl, methoxy, ethoxy, trifluoromethyl, trifluoromethoxy, cyano and nitro, represents benzyl which is unsubstituted or mono- or disubstituted by identical or different substituents from the group consisting of fluorine, chlorine, bromine, methyl, ethyl, propyl, i-propyl, methoxy, ethoxy, trifluoromethyl and trifluoromethoxy, represents thienyl, furanyl or pyridyl, each of which is unsubstituted or mono- or disubstituted by identical or different substituents from the group consisting of fluorine, chlorine, bromine, methyl and ethyl, represents phenoxy-$C_1$–$C_4$-alkyl which is unsubstituted or mono- or disubstituted by identical or different substituents from the group consisting of fluorine, chlorine, methyl and ethyl, or represents pyridyloxy-$C_1$–$C_4$-alkyl, pyrimidyloxy-$C_1$–$C_4$-alkyl or thiazolyloxy-$C_1$–$C_4$-alkyl, each of which is unsubstituted or mono- or disubstituted by identical or different substituents from the group consisting of fluorine, chlorine, amino, methyl and ethyl, $R^2$ represents $C_1$–$C_{14}$-alkyl, $C_2$–$C_6$-alkenyl, $C_1$–$C_4$-alkoxy-$C_2$–$C_6$-alkyl or poly-$C_1$–$C_4$-alkoxy-$C_2$–$C_6$-alkyl, each of which is unsubstituted or mono- to pentasubstituted by identical or different substituents from the group consisting of fluorine and chlorine, represents $C_3$–$C_6$-cycloalkyl which is unsubstituted or mono- to trisubstituted by identical or different substituents from the group consisting of fluorine, chlorine, methyl, ethyl, methoxy and ethoxy, or represents phenyl or benzyl, each of which is unsubstituted or mono- or disubstituted by identical or different substituents from the group consisting of fluorine, chlorine, nitro, cyano, methyl, ethyl, propyl, i-propyl, methoxy, ethoxy, trifluoromethoxy and trifluoromethyl, $R^3$ represents $C_1$–$C_6$-alkyl, which is unsubstituted or mono- to trisubstituted by identical or different substituents from the group consisting of fluorine and chlorine, or represents phenyl or benzyl, each of which is unsubstituted or mono- or disubstituted by fluorine, chlorine, bromine, methyl, ethyl, methoxy, ethoxy, trifluoromethyl, trifluoromethoxy, cyano or nitro, $R^4$ and $R^5$ independently of one another each represent $C_1$–$C_4$-alkyl, $C_1$–$C_4$-alkoxy, $C_1$–$C_4$-alkylamino, di-($C_1$–$C_4$-alkyl)-amino, $C_1$–$C_4$-alkylthio, each of which is unsubstituted or mono- to trisubstituted by identical or different substituents from the group consisting of fluorine and chlorine, or represents phenyl, phenoxy or phenylthio, each of which is unsubstituted or mono- or disubstituted by identical or different substituents from the group consisting of fluorine, chlorine, bromine, nitro, cyano, $C_1$–$C_2$-alkoxy, trifluoromethoxy, $C_1$–$C_2$-alkylthio, trifluoromethyl or $C_1$–$C_3$-alkyl, $R^6$ represents hydrogen, represents $C_1$–$C_6$-alkyl, $C_1$–$C_6$-alkoxy-$C_2$–$C_4$-alkyl, each of which is unsubstituted or mono- to trisubstituted by identical or different substituents from the group consisting of fluorine and chlorine, represents $C_3$–$C_6$-cycloalkyl which is unsubstituted or mono- or disubstituted by identical or different substituents from the group consisting of fluorine, chlorine, methyl, methoxy, trifluoromethyl and trifluoromethoxy, represents phenyl which is unsubstituted or mono- or disubstituted by identical or different substituents from the group consisting of fluorine, chlorine, trifluoromethyl, $C_1$–$C_4$-alkyl, trifluoromethoxy and $C_1$–$C_4$-alkoxy, or represents benzyl which is unsubstituted or mono- or disubstituted by identical or different substituents from the group consisting of fluorine, chlorine, $C_1$–$C_4$-alkyl, trifluoromethyl, trifluoromethoxy and $C_1$–$C_4$-alkoxy, $R^7$ represents hydrogen, or represents $C_1$–$C_6$-alkyl or $C_3$–$C_6$-alkenyl, each of which is unsubstituted or mono- to trisubstituted by identical or different substituents from the group consisting of fluorine and chlorine, or $R^6$ and $R^7$ combine with the linking N-atom to form an a 5- to 7-membered ring containing or not containing oxygen- or sulphur and unsubstituted or substituted methyl.

4. A process for preparing a compound of the formula (I) according to claim 1, wherein (A) a compound of the formula (Ia)

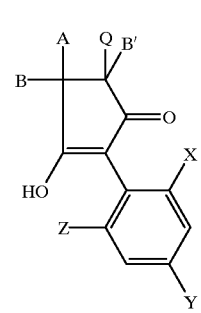

(Ia)

in which

A, B, B', Q, X, Y and Z are each as defined in claim 1, is obtained when a compound of the formula (II)

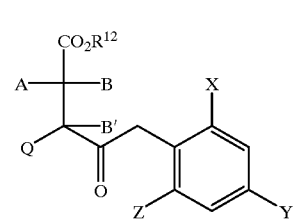

(II)

in which

A, B, B' Q, X, Y and Z are each as defined above, and $R^{12}$ represents alkyl is condensed intramolecularly in the presence of a diluent and in the presence of a base;

(B) a compound of the formula (Ib)

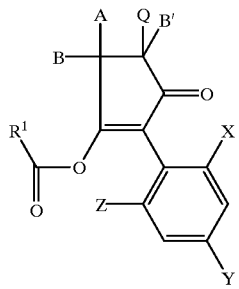
(Ib)

in which
A, B, B', Q, X, Y, Z and R¹ are each as defined in claim 1
is obtained
when a compound of the formula (Ia)

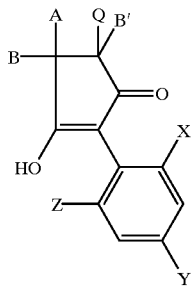
(Ia)

in which
A, B, B', X, Y, Z and Q are each as defined above
is reacted

α) with an acyl halide of the formula (III)

(III)

in which
R¹ is as defined above and
Hal represents halogen,
in the absence or presence of a diluent and in the absence or presence of an acid binding agent;
or β) with a carboxylic anhydride of the formula (IV)

R¹—CO—O—CO—R¹ (IV)

in which
R¹ is as defined above,
in the absence or presence of a diluent and in the absence or presence of an acid binding agent;

(C) a compound of the formula (Ic-1)

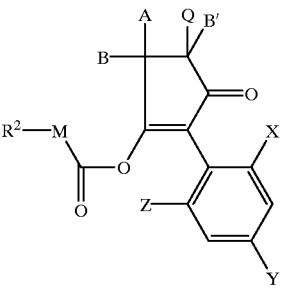
(Ic-1)

in which
A, B, B', Q, X, Y, Z and R² are as defined in claim 1
and
M represents oxygen or sulphur
is obtained
when a compound of the formula (Ia)

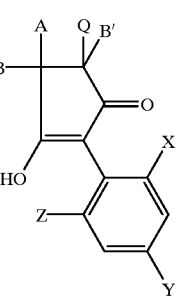
(Ia)

in which
A, B, B', Q, X, Y and Z are each as defined above
is reacted with a chloroformic ester or a chloroformic thioester of the formula (V)

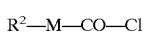
R²—M—CO—Cl (V)

in which
R² and M are each as defined above,
in the absence or presence of a diluent and in the absence or presence of an acid binding agent;

(D) a compound of the formula (Ic-2)

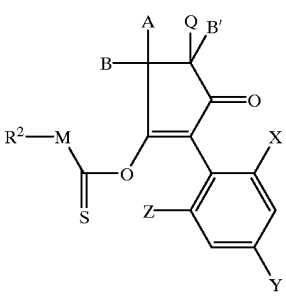
(Ic-2)

in which
A, B, B', Q, X, Y, Z and R² are each as defined in claim 1,
and
M represents oxygen or sulphur,
is obtained, when a compound of the formula (Ia)

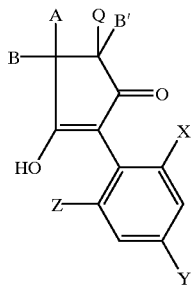
(Ia)

in which
A, B, B', Q, X, Y and Z are each as defined above
is reacted

α) with a chloromonothioformic ester or a chlorodithioformic ester of the formula (VI)

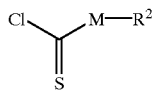
(VI)

in which
M and R² are each as defined above,
in the absence or presence of a diluent and in the absence or presence of an acid binding agent;
or β) with carbon disulphide and then with an alkyl halide of the formula (VII)

R²—Hal (VII)

in which
R² is as defined above
and
Hal represents chlorine, bromine or iodine,
in the absence or presence of a diluent and in the absence or presence of a base;

(E) a compound of the formula (Id)

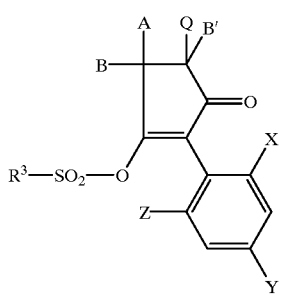
(Id)

in which
A, B, B', Q, X, Y, Z and R³ are each as defined in claim 1,
is obtained when a compound of the formula (Ia)

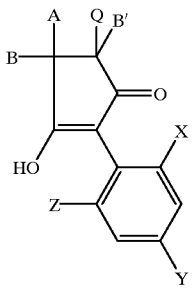
(Ia)

in which
A, B, B', Q, X, Y and Z are each as defined above
is reacted with a sulphonyl chloride of the formula (VIII)

R³—SO₂—Cl (Vm)

in which
R³ is as defined above,
in the absence or presence of a diluent and in the absence or presence of an acid binding agent;

(F) a compound of the formula (Ie)

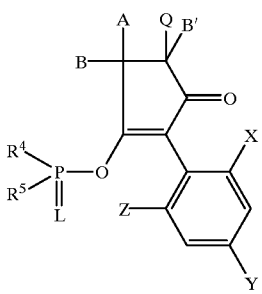
(Ie)

in which
A, B, L, B', Q, X, Y, Z, R⁴ and R⁵ are each as defined in claim 1
is obtained
when a compound of the formula (Ia) or an enol thereof

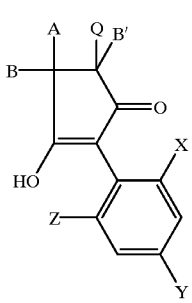
(Ia)

in which
A, B, B' Q, X, Y and Z are each as defined above
is reacted with a phosphorus compound of the formula (IX)

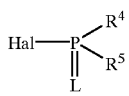

in which
L, $R^4$ and $R^5$ are each as defined above
and
Hal represents halogen,
in the absence or presence of a diluent and in the absence or presence of an acid binding agent;
(G) a compound of the formula (If)

(If)

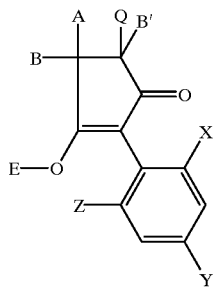

in which
A, B, B' Q, X, Y and Z are each as defined in claim 1
and
E represents a metal ion equivalent or represents an ammonium ion
is obtained
when a compound of the formula (Ia)

(Ia)

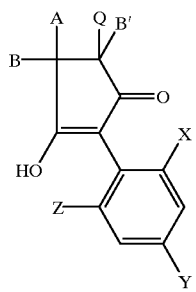

in which
A, B, B', Q, X, Y and Z are each as defined above
is reacted with a metal compound or an amine of the formulae (X) and (XI), respectively

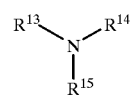

(X)

$MeR_t^{16}$ (XI)

$R^{13}$—N($R^{15}$)—$R^{14}$ in which
Me represents mono- or bivalent metal ions,
t represents the number 1 or 2, $R^{13}$, $R^{14}$ and $R^{15}$ independently of one another each represent hydrogen or alkyl and
$R^{16}$ represents hydrogen, hydroxyl or $C_1$–$C_4$-alkoxy,
in the absence or presence of a diluent;
(H) a compound of the formula (Ig)

(Ig)

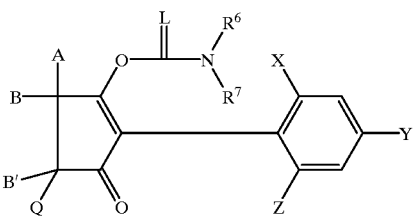

in which
A, B, L, B', Q, X, Y, Z, $R^6$ and $R^7$ are each as defined in claim 1
is obtained when a compound of the formula (Ia)

(Ia)

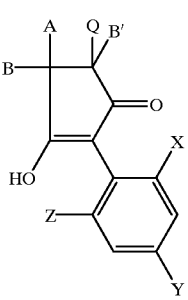

in which
A, B, B', Q, X, Y and Z are each as defined above
is reacted
α) with a compound of the formula (XII)

$R^6$—N=C=L  (XII)

in which
L and $R^6$ are each as defined above,
in the absence or presence of a diluent and in the absence or presence of a catalyst,
or
β) with a carbamoyl chloride or thiocarbamoyl chloride of the formula (XIII)

(XIII)

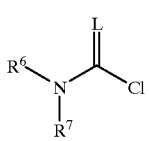

in which
L, $R^6$ and $R^7$ are each as defined above
in the absence or presence of a diluent and in the absence or presence of an acid binding agent.

5. A pesticidal composition comprising a pesticidally effective amount of at least one compound of the formula (I) according to claim 1 and an extender.

6. Method for controlling pests comprising applying a pesticidally effective amount of at least one compound according to claim 1, to the pests to their habitat or to an area from which it is desired to exclude such pests.

7. A process for preparing pesticidal compositions comprising mixing at least one compound of the formula (I) according to claim 1 with extenders or surfactants or extenders and surfactants.

8. A herbicidal composition, comprising a herbicidally effective amount of at least one compound of the formula (I) according to claim 1 and an extender.

9. A method controlling weeds comprising applying a herbicidally effective amount of at least one compound according to claim 1, to the weeds to their habitat or to an area from which it is desired to exclude such weeds.

10. A process for preparing herbicidal compositions comprising mixing at least one compound of the formula (I) according to claim 1 with extenders or surfactants or extenders and surfactants.

\* \* \* \* \*

UNITED STATES PATENT AND TRADEMARK OFFICE
CERTIFICATE OF CORRECTION

PATENT NO.   : 6,515,184 B1
DATED        : February 4, 2003
INVENTOR(S)  : Reiner Fischer et al.

It is certified that error appears in the above-identified patent and that said Letters Patent is hereby corrected as shown below:

Column 62,
Line 21, change "ftiranyl" to -- furanyl --
Line 36, change "$R^2$ represents $C_1$ -$C_6$-alkyl" to -- $R^2$ represents $C_1$ -$C_{16}$-alkyl --

Signed and Sealed this

Tenth Day of June, 2003

JAMES E. ROGAN
*Director of the United States Patent and Trademark Office*